United States Patent
Sadakane et al.

(10) Patent No.: US 11,045,152 B2
(45) Date of Patent: Jun. 29, 2021

(54) X-RAY TOMOGRAPHY APPARATUS AND X-RAY TOMOGRAPHY METHOD

(71) Applicant: J. MORITA MANUFACTURING CORPORATION, Kyoto (JP)

(72) Inventors: Tomoyuki Sadakane, Kyoto (JP); Yuu Nishimura, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 115 days.

(21) Appl. No.: 16/487,835

(22) PCT Filed: Feb. 23, 2018

(86) PCT No.: PCT/JP2018/006716
§ 371 (c)(1),
(2) Date: Aug. 22, 2019

(87) PCT Pub. No.: WO2018/155632
PCT Pub. Date: Aug. 30, 2018

(65) Prior Publication Data
US 2021/0093282 A1 Apr. 1, 2021

(30) Foreign Application Priority Data
Feb. 23, 2017 (JP) .............................. JP2017-031727

(51) Int. Cl.
*A61B 6/02* (2006.01)
*A61B 6/14* (2006.01)
(Continued)

(52) U.S. Cl.
CPC .............. *A61B 6/027* (2013.01); *A61B 6/025* (2013.01); *A61B 6/035* (2013.01); *A61B 6/14* (2013.01);
(Continued)

(58) Field of Classification Search
None
See application file for complete search history.

(56) References Cited

U.S. PATENT DOCUMENTS 6,814,489 B2 * 11/2004 Jensen ..................... A61B 6/08
378/197
9,833,215 B2 * 12/2017 Stopp ....................... A61N 5/01
(Continued)

FOREIGN PATENT DOCUMENTS

EP 3590432 A1 1/2020
JP 11-290307 A 10/1999
(Continued)

OTHER PUBLICATIONS

Search Report from the corresponding European Patent Application No. 18757460.3 dated Oct. 2, 2020.
(Continued)

*Primary Examiner* — Thomas R Artman
(74) *Attorney, Agent, or Firm* — Shinjyu Global IP

(57) ABSTRACT

By turning an X-ray generator and an X-ray detector around a head of a subject, an imaging region is irradiated with an X-ray beam from a plurality of directions to obtain an X-ray projection image. When a center axis X-ray of the X-ray beam passing through a turning center axis is orthogonal to a tomographic layer of interest, the X-ray detector is caused to approach the tomographic layer of interest while the X-ray generator is moved away from the tomographic layer of interest as compared to when the center axis X-ray is not orthogonal to a tomographic layer of interest.

11 Claims, 22 Drawing Sheets

(51) Int. Cl.
*A61B 6/03* (2006.01)
*A61B 6/00* (2006.01)

(52) U.S. Cl.
CPC .......... *A61B 6/4441* (2013.01); *A61B 6/4452* (2013.01); *A61B 6/4476* (2013.01); *A61B 6/469* (2013.01); *A61B 6/5205* (2013.01); *A61B 6/547* (2013.01)

(56) References Cited

U.S. PATENT DOCUMENTS

| | | | |
|---|---|---|---|
| 10,874,360 B2* | 12/2020 | Nishimura | A61B 6/02 |
| 2003/0099328 A1* | 5/2003 | Jensen | A61B 6/466 |
| | | | 378/198 |
| 2005/0117693 A1 | 6/2005 | Miyano | |
| 2010/0067650 A1 | 3/2010 | Arai et al. | |
| 2014/0254750 A1 | 9/2014 | Yoshimura et al. | |
| 2015/0265231 A1 | 9/2015 | Stopp et al. | |
| 2020/0008760 A1* | 1/2020 | Nishimura | A61B 6/542 |

FOREIGN PATENT DOCUMENTS

| | | | | | |
|---|---|---|---|---|---|
| JP | 2005-510278 | A | | 4/2005 | |
| JP | 2007-526104 | A | | 9/2007 | |
| JP | 2010-503510 | A | | 2/2010 | |
| JP | 2010-075682 | A | | 4/2010 | |
| JP | 2014-195644 | A | | 10/2014 | |
| JP | 2015-530166 | A | | 10/2015 | |
| JP | 2018134288 | A | * | 8/2018 | ............... A61B 6/14 |
| JP | 2018143335 | A | * | 9/2018 | ............... A61B 6/02 |
| WO | 03/045242 | A1 | | 6/2003 | |
| WO | 2007/018333 | A1 | | 2/2007 | |
| WO | 2008/035828 | A1 | | 3/2008 | |
| WO | 2015125589 | A1 | | 8/2015 | |

OTHER PUBLICATIONS

Search Report from the corresponding International Patent Application No. PCT/JP2018/006716 dated May 29, 2018.

* cited by examiner

FIG. 1
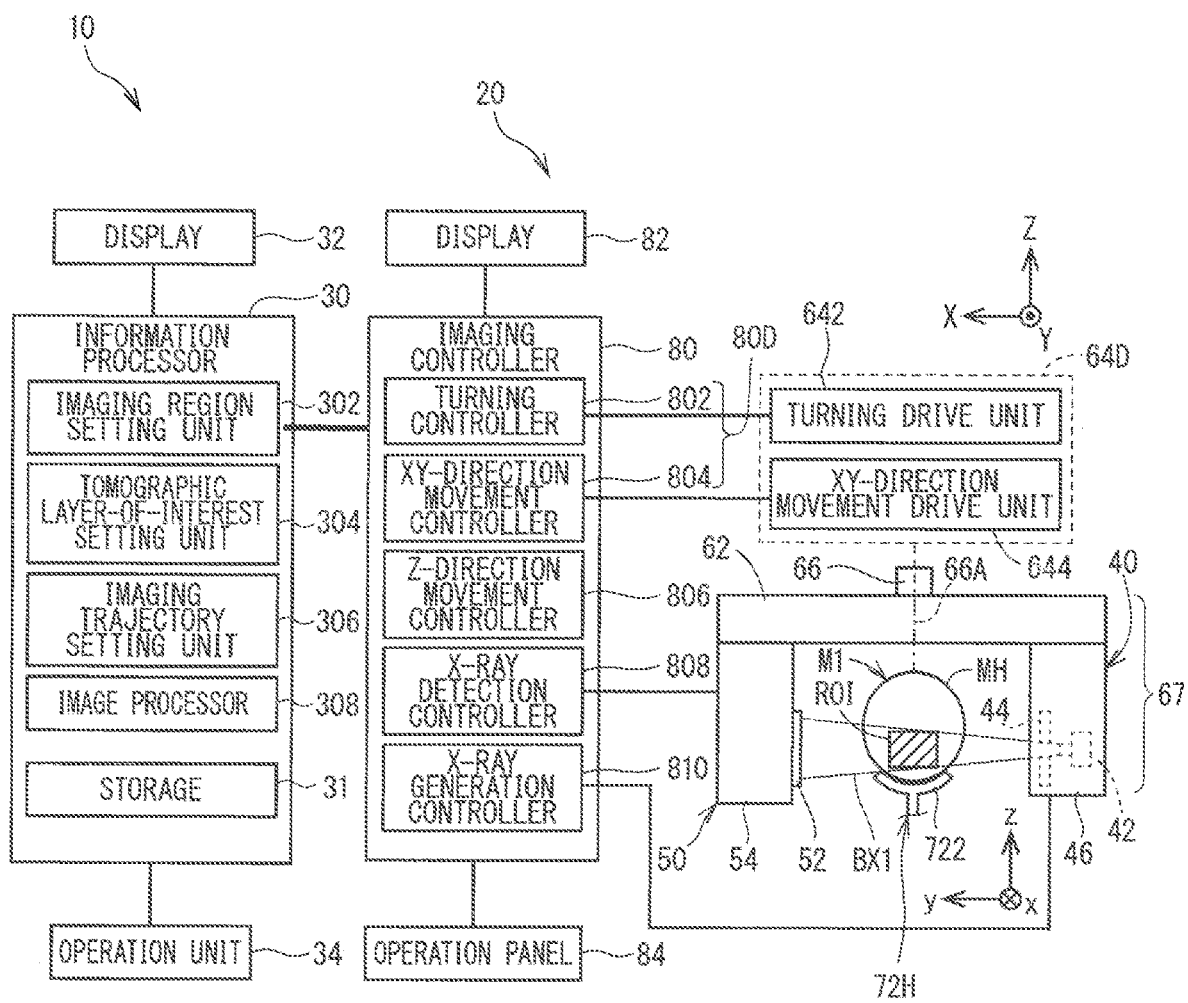
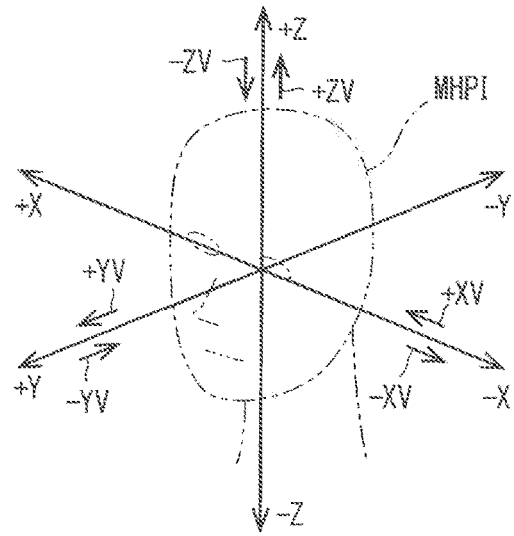

F I G. 13
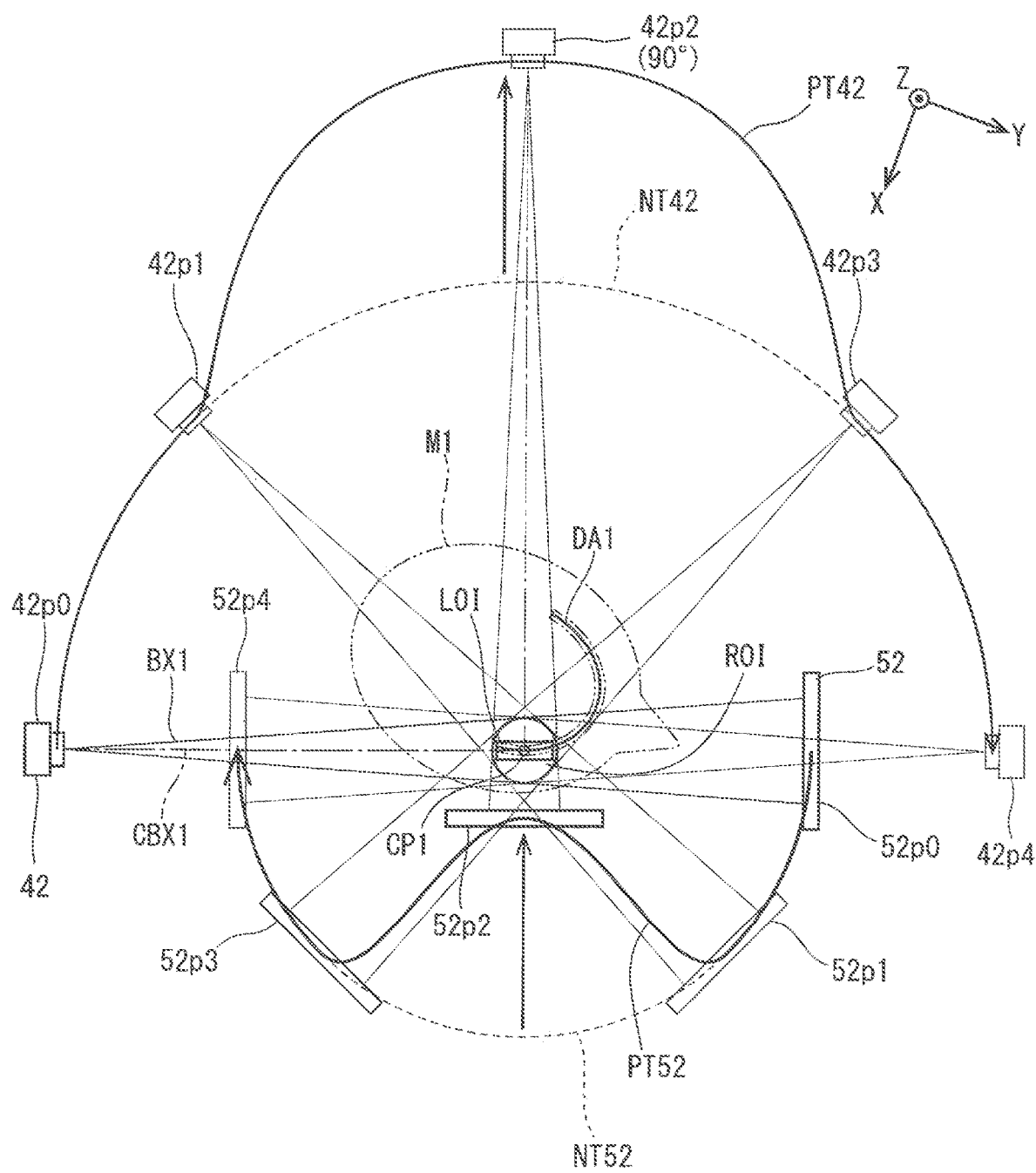

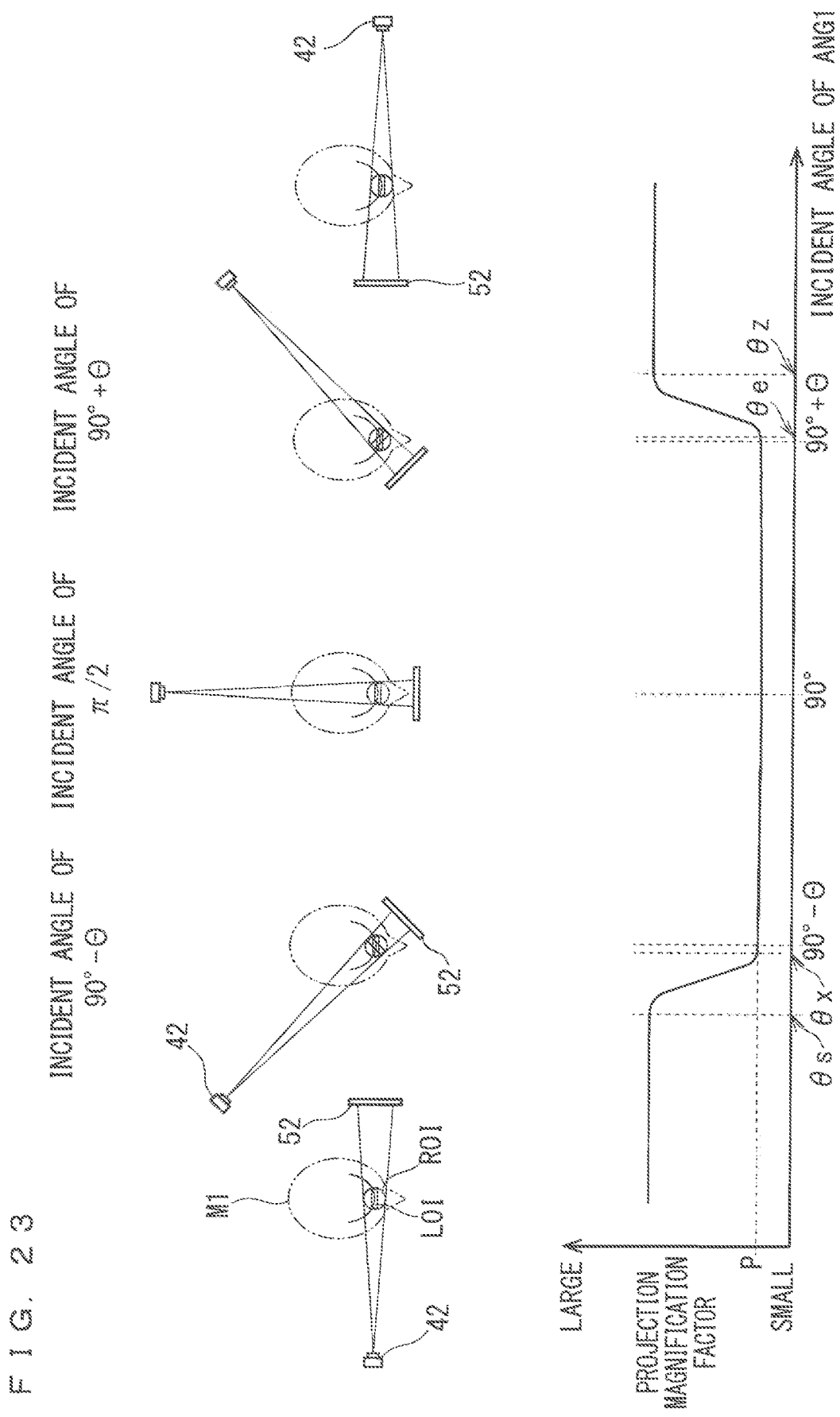

X-RAY TOMOGRAPHY APPARATUS AND X-RAY TOMOGRAPHY METHOD

CROSS-REFERENCE TO RELATED APPLICATIONS

This application is the National Phase in the United States of PCT/JP2018/006716, filed Feb. 23, 2018, which claims priority to Japanese Patent Application No. 2017-031727, filed Feb. 23, 2017. Those applications are incorporated by reference in their entireties.

TECHNICAL FIELD

The present invention relates to a technique of performing X-ray tomography to acquire a tomographic image of a tomographic layer of interest.

BACKGROUND ART

An X-ray CT (computed tomography) imaging apparatus that performs tomographic imaging on any site of a human body is widely known in the field of medical X-ray diagnosis. In the X-ray CT imaging apparatus, image information (an X-ray projection image or a transmission image) is acquired by rotating an X-ray generator and an X-ray detector, which are disposed opposite to each other, around a subject. Image processing is performed on the obtained image information to generate a tomographic image indicating a tomographic plane obtained by cutting any site such as a head and a body.

Japanese Patent Application Publication No. 2010-075682 discloses a technique of performing CT imaging by reducing an influence of a high X-ray absorption site existing in the subject using a control model based on high X-ray absorption site information existing in the subject. Specifically, at least one of an increase in X-ray output and a decrease in turning speed is performed at timing at which an X-ray cone beam reaches the high X-ray absorption site (for example, a cervical spine). In Japanese Patent Application Publication No. 2010-075682, a clear tomographic image is obtained by reducing the influence of the high X-ray absorption site.

BRIEF SUMMARY

However, in the case of Japanese Patent Application Publication No. 2010-075682, there is a possibility that an exposure dose of the subject is increased more than usual by increasing the X-ray output or decreasing the turning speed. Because the increase in the exposure dose is not desirable, there is a demand for an alternative technique of acquiring a clear tomographic image.

It is considered that resolution of the X-ray projection image depends on resolving power of the X-ray detector and a size of a focal plane of the X-ray. From the viewpoint of the resolving power of the X-ray detector, a magnification factor of the X-ray projection image is desirably enlarged as much as possible. On the other hand, it is known that blurring occurs in the X-ray projection image due to the fact that the focal plane of the X-ray has a certain size. The blurring caused by the focal plane also increases with increasing magnification factor of the X-ray projection image. For this reason, for a general X-ray detector, a clear (that is, high-resolution) X-ray projection image can be acquired by decreasing the magnification factor as much as possible (by bringing the magnification factor close to 1).

As a specific means for decreasing the magnification factor, it is conceivable to bring the X-ray detector close to the subject or to move the X-ray generator away from the subject. However, when the X-ray detector is turned while approaching the subject, a turning radius of the X-ray detector can be decreased, which can cause the X-ray detector to contact with the subject. On the other hand, when the X-ray generator is turned while separated from the subject, the turning radius of the X-ray generator can be increased, which can cause the X-ray generator to collide with a peripheral member. There is a need for an imaging technique of decreasing the magnification factor without interfering with the turning of the X-ray generator and the X-ray detector.

The present invention has been made in view of the above problems, and an object of the present invention is to provide a technique of acquiring a high-resolution X-ray projection image without affecting the turning of the X-ray generator and the X-ray detector.

In order to solve the above problem, according to a first aspect, an X-ray tomography apparatus includes: an X-ray generator that emits an X-ray beam; an X-ray detector that detects the X-ray beam emitted from the X-ray generator; a support that supports the X-ray generator and the X-ray detector; a tomographic layer-of-interest setting unit that sets a tomographic layer of interest; a turning drive unit that turns the X-ray generator and the X-ray detector relative to the tomographic layer of interest about a turning center axis set between the X-ray generator and the X-ray detector; a movement drive unit that moves at least one of the X-ray generator and the X-ray detector relative to the tomographic layer of interest in a direction perpendicular to the turning center axis; an image processor that generates an X-ray tomographic image indicating the tomographic layer of interest by performing image processing on a plurality of X-ray projection images generated based on an output signal output from the X-ray detector; and a controller that controls the turning drive unit and the movement drive unit. When a center axis X-ray passing through the turning center axis in the X-ray beam is orthogonal to the tomographic layer of interest, the controller causes the X-ray detector to relatively approach the tomographic layer of interest and/or to relatively move the X-ray generator away from the tomographic layer of interest as compared to when the center axis X-ray is not orthogonal to the tomographic layer of interest.

A second aspect is the X-ray tomography apparatus of the first aspect, in which the support includes a turning arm that supports the X-ray generator at one end side while supporting the X-ray detector at the other end side, and the turning drive unit turns the turning arm via a shaft, the shaft being connected to a position between the X-ray generator and the X-ray detector in the turning arm.

A third aspect is the X-ray tomography apparatus of the second aspect, in which the movement drive unit moves the shaft of the turning arm in the direction perpendicular to the turning center axis.

A fourth aspect is the X-ray tomography apparatus of any one of the first to third aspects, in which the controller starts at least one of the approach of the X-ray detector to the tomographic layer of interest and the movement of the X-ray generator away from the tomographic layer of interest before the center axis X-ray becomes orthogonal to the tomographic layer of interest, and the controller starts at least one of the movement of the X-ray detector away from the tomographic layer of interest and the approach of the X-ray generator to the tomographic layer of interest after the center axis X-ray becomes orthogonal to the tomographic layer of interest.

A fifth aspect is the X-ray tomography apparatus of any one of the first to fourth aspects, which further includes an imaging region setting unit that sets designation of an imaging region in which a plurality of X-ray projection images are acquired by irradiation of the X-ray beam from a plurality of directions based on an input operation of designation through an operation unit.

A sixth aspect is the X-ray tomography apparatus of the fifth aspect, in which the tomographic layer-of-interest setting unit sets the tomographic layer of interest according to the imaging region set by the imaging region setting unit.

A seventh aspect is the X-ray tomography apparatus of the sixth aspect, in which the operation unit receives designation of the imaging region so as to include a part of a dental arch, and the tomographic layer-of-interest setting unit sets a tomographic layer along said part of the dental arch included in the imaging region as the tomographic layer of interest.

An eighth aspect is the X-ray tomography apparatus of any one of the first aspect to the seventh aspect, in which the image processor performs image processing after matching magnification factors of the plurality of X-ray projection images with each other, and generates the X-ray tomographic image.

A ninth aspect is the X-ray tomography apparatus of any one of the first aspect to the eighth aspect, which further includes a tomographic thickness designation receiving unit that receives designation of a tomographic thickness of the tomographic layer of interest. The controller determines an incident angle when the X-ray detector is caused to approach the tomographic layer of interest according to the designated tomographic thickness.

According to a tenth aspect of the present invention, an X-ray tomography method includes: (a) a step of setting a tomographic layer of interest; (b) a step of turning an X-ray generator and an X-ray detector relative to the tomographic layer of interest around a turning center axis set between the X-ray generator and the X-ray detector while the tomographic layer of interest is disposed between the X-ray generator and the X-ray detector; (c) a step of detecting an X-ray beam emitted from the X-ray generator using the X-ray detector in the step (b); (d) a step of causing, when a center axis X-ray passing through the turning center axis in the X-ray beam is orthogonal to the tomographic layer of interest in the step (b), the X-ray detector to relatively approach the tomographic layer of interest and/or to relatively move the X-ray generator away from the tomographic layer of interest as compared to when the center axis X-ray is not orthogonal to the tomographic layer of interest; and (e) a step of performing image-processing on a plurality of X-ray projection images generated based on an output signal output from the X-ray detector in the step (c), and generating an X-ray tomographic image indicating the tomographic layer of interest.

According to an eleventh aspect of the present invention, an X-ray tomography apparatus includes: an X-ray generator that emits an X-ray beam; an X-ray detector that detects the X-ray beam emitted from the X-ray generator; a support that supports the X-ray generator and the X-ray detector; a tomographic layer-of-interest setting unit that sets a tomographic layer of interest; a turning drive unit that turns the X-ray generator and the X-ray detector relative to the tomographic layer of interest about a turning center axis set between the X-ray generator and the X-ray detector; a movement drive unit that moves at least one of the X-ray generator and the X-ray detector relative to the tomographic layer of interest in a direction perpendicular to the turning center axis; an image processor that generates an X-ray tomographic image indicating the tomographic layer of interest by performing image processing on a plurality of X-ray projection images generated based on an output signal output from the X-ray detector; and a controller that controls the movement drive unit according to an incident angle while controlling the turning drive unit to change the incident angle of the X-ray beam with respect to the tomographic layer of interest. The controller controls movement of at least one of the X-ray generator and the X-ray detector such that a magnification factor is relatively decreased in a state in which a irradiation axis of the X-ray beam is incident on the tomographic layer of interest in a confronting manner when the state in which the irradiation axis of the X-ray beam is incident on the tomographic layer of interest in the confronting manner and a state in which the irradiation axis of the X-ray beam is incident on the tomographic layer of interest in a non-confronting manner are compared to each other, while the X-ray generator and the X-ray detector are turned.

According to the X-ray tomography apparatus of the first aspect, when the center axis X-ray of the X-ray beam is orthogonal to the tomographic layer of interest, the X-ray detector is caused to approach the tomographic layer of interest or the X-ray detector is moved away from the tomographic layer of interest as compared to when the center axis X-ray is not orthogonal to the tomographic layer of interest, which allows the magnification factor of the X-ray projection image to be decreased in the X-ray detector. Consequently, the blurring caused by the influence of the focal size of the X-ray is reduced on the X-ray projection image that is obtained when the X-ray generator confronts the tomographic layer of interest, so that the resolution of the X-ray projection image can be improved.

In addition, the X-ray detector is caused to approach the tomographic layer of interest by limiting the X-ray generator and the X-ray detector to a part of the turning angle during turning of the X-ray generator and the X-ray detector relative to the subject, which prevents the X-ray detector from contacting with the subject. Alternatively, the X-ray generator can be prevented from colliding with another member by moving the X-ray generator away from the tomographic layer of interest.

According to the X-ray tomography apparatus of the second aspect, the turning arm is turned via the shaft, which allows the X-ray generator and the X-ray detector to be integrally turned.

According to the X-ray tomography apparatus of the third aspect, by moving the shaft, the X-ray detector can be moved together with the X-ray generator in a direction in which the X-ray detector is caused to approach to and moved away from the tomographic layer of interest. Consequently, the magnification factor of the projection image projected onto the X-ray detector can be changed.

According to the X-ray tomography apparatus of the fourth aspect, the magnification factor can be decreased before the center axis X-ray becomes orthogonal to the tomographic layer of interest, namely, until the X-ray generator becomes the confronting state. After the X-ray generator becomes the confronting state, the X-ray detector is moved away from the tomographic layer of interest or the X-ray generator is caused to approach the tomographic layer of interest, which prevents the X-ray detector from contacting with the subject, or which prevents the X-ray generator from colliding with a peripheral member.

According to the X-ray tomography apparatus of the fifth aspect, an operator can designate an imaging region irradiated with the X-rays in the subject.

According to the X-ray tomography apparatus of the sixth aspect, the tomographic layer of interest is automatically set according to the set imaging region, so that the operator can eliminate the operation to set the tomographic layer of interest.

According to the X-ray tomography apparatus of the seventh aspect, when the imaging region is set so as to include the dental arch, the tomographic layer of interest is set along the dental arch. Consequently, the tomographic image of the tomographic layer of interest suitable for a dental diagnosis can be acquired. The dental arch is unevenly distributed in front of the head, and extends along a front edge of the head. For this reason, when the X-ray generator confronts the tomographic layer of interest set along the dental arch, the X-ray detector can be caused to approach the tomographic layer of interest without touching with the head. Thus, the high-resolution X-ray tomographic image can easily be obtained for the tomographic layer of interest in a part of the dental arch.

According to the X-ray tomography apparatus of the eighth aspect, by previously matching the magnification factors of the plurality of X-ray projection images with each other, positions onto which each point in the imaging region is projected can be matched with each other in the plurality of X-ray projection images. Consequently, parallelization of arithmetic processing is promoted, so that time necessary for the arithmetic processing can be shortened when an arithmetic processing apparatus such as a GPU excellent in parallel processing is used.

According to the X-ray tomography apparatus of the ninth aspect, the suitable incident angle is determined according to the designated tomographic thickness when the magnification factor is changed. Consequently, the X-ray tomographic image indicating the tomographic layer of interest having the designated tomographic thickness can suitably be acquired.

According to the X-ray tomography method of the tenth aspect, when the center axis X-ray of the X-ray beam is orthogonal to the tomographic layer of interest, the X-ray detector is caused to approach the tomographic layer of interest or the X-ray generator is moved away from the tomographic layer of interest as compared to when the center axis X-ray is not orthogonal to the tomographic layer of interest. Consequently, the magnification factor of the X-ray projection image projected onto the X-ray detector can be decreased. Consequently, the blurring caused by the influence of the focal size of the X-ray is reduced on the X-ray projection image that is obtained when the X-ray generator confronts the tomographic layer of interest, so that the resolution of the X-ray projection image can be improved.

In addition, the X-ray detector is caused to approach the tomographic layer of interest by limiting the X-ray generator and the X-ray detector to a part of the turning angle during turning of the X-ray generator and the X-ray detector relative to the subject, which prevents the X-ray detector from contacting with the subject. Alternatively, the X-ray generator can be prevented from colliding with another member by moving the X-ray generator away from the tomographic layer of interest.

According to the X-ray tomography apparatus of the eleventh aspect, movement of at least one of the X-ray generator and the X-ray detector is controlled while the irradiation axis of the X-ray beam is incident on the tomographic layer of interest in the confronting manner, which allows the magnification factor of the X-ray projection image to be decreased in the X-ray detector when the state in which the irradiation axis of the X-ray beam is incident on the tomographic layer of interest in the confronting manner is compared with the state in which the irradiation axis is incident on the tomographic layer of interest in the non-confronting manner. Consequently, the blurring caused by the influence of the focal size of the X-ray is reduced on the X-ray projection image that is obtained when the irradiation axis of the X-ray beam is incident on the tomographic layer of interest in the confronting manner, so that the resolution of the X-ray projection image can be improved.

BRIEF DESCRIPTION OF THE DRAWINGS

FIG. 1 is a view illustrating a configuration of an X-ray tomography apparatus 10 according to an embodiment.

FIG. 13 is a view illustrating an example of the X-ray imaging.

FIG. 23 is a view illustrating the fluctuation in the projection magnification factor according to an incident angle ANG1.

DETAILED DESCRIPTION

Figure 2:
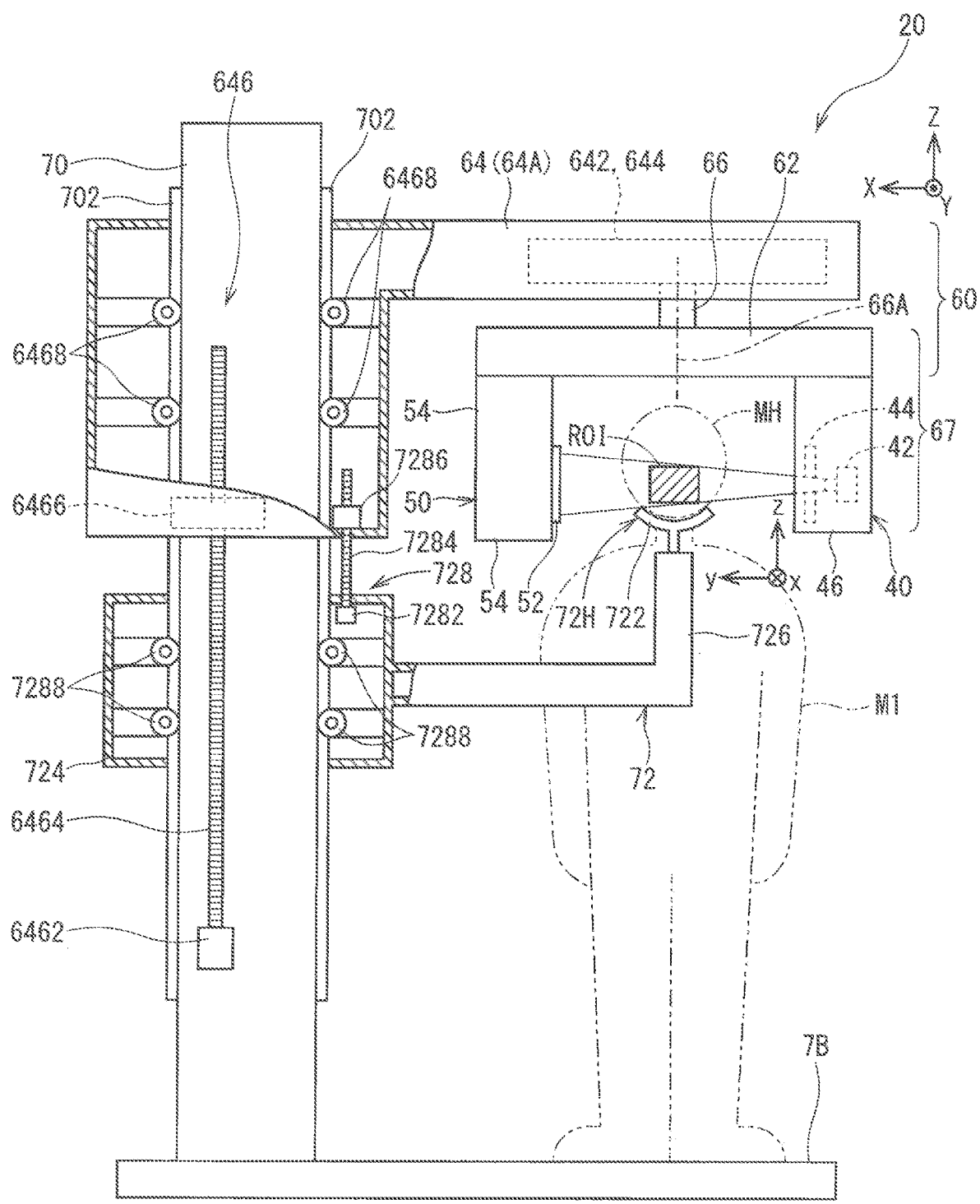
FIG. 2 is a side view schematically illustrating an imaging unit 20 of the embodiment.

Hereinafter, an embodiment of the present invention will be described with reference to the accompanying drawings. Constituent elements described in the embodiment are merely examples, and the scope of the present invention is not limited to the constituent elements of the embodiment. In the drawings, for ease of understanding, sometimes dimensions and the number of each portion can be exaggerated or simplified as necessary.

1. EMBODIMENT

Figure 3:
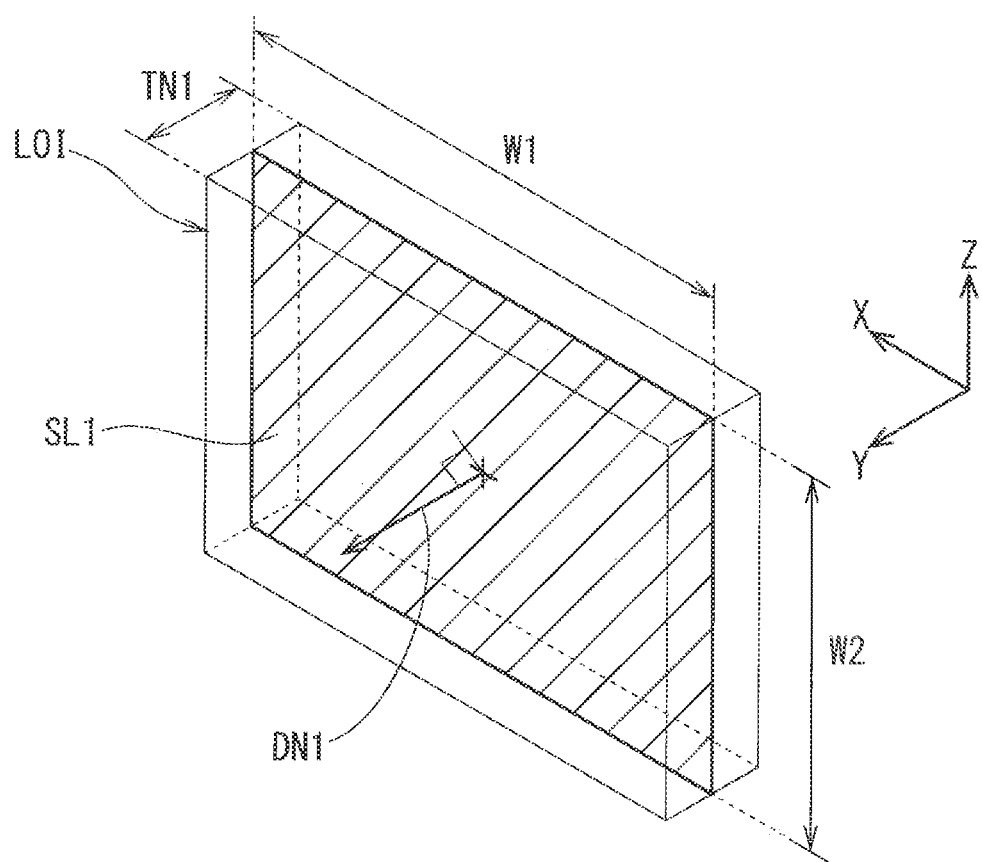
FIG. 3 is a view conceptually illustrating a tomographic layer of interest LOI of the embodiment.

FIG. 1 is a view illustrating a configuration of an X-ray tomography apparatus 10 according to an embodiment. FIG. 2 is a side view schematically illustrating an imaging unit 20 of the embodiment. FIG. 3 is a view conceptually illustrating a tomographic layer of interest LOI of the embodiment.

A right-handed XYZ (X-axis, Y-axis, Z-axis) orthogonal coordinate system and a right-handed xyz (x-axis, y-axis, z-axis) orthogonal coordinate system are defined in FIG. 1. Because a supporting relationship of a post 70 and a support 60 will be described in detail later, the detailed description is not made here, but the supporting relationship will be described in the minimum necessary range for explanation of each axial direction of a coordinate.

The post 70 is erected on a base 7B placed on a ground on which the imaging unit 20 is installed, and an upper frame 64 includes a base end at a portion contacting with the post 70, and extends in one direction crossing a longitudinal direction of the post 70 from the base end. The upper frame 64 pivotally supports a turning unit 67 via a shaft 66. A turning axis 66A about which a turning arm 62 turns mechanically passes through the shaft 66. The axial direction of the turning axis 66A is a Z-axis direction.

The X-ray tomography apparatus 10 in FIG. 1 is a standing type imaging apparatus. The Z-axis direction is a vertical direction, and is made to coincide with a body axis direction of a subject M1 positioned in the imaging unit 20. An arm 726 of a subject holder 72 has a base end in a portion contacting with the post 70, and extends in the same direction as the upper frame 64 from the base end. A head MH of the subject M1 is supported by a head support 72H such as a chin rest 722 provided on a leading end side of the arm 726. The post 70 extends in the Z-axis direction with respect to the base 7B. The base 7B spreads on the ground, and extends to at least a foot of the subject M1.

In the present application, each direction is defined on the assumption that the head MH is positioned and supported at a defined regular location by the head support 72H while facing in a regular direction. A front-rear direction of the head MH is a Y-axis direction, and a left-right direction of the head MH is an X-axis direction. Sometimes the Z-axis direction is referred to as a Z-direction, a Y-axis direction is referred to as a Y-direction, and an X-axis direction is referred to as an X-direction. A front of the head MH, namely, the surface of the imaging unit 20 viewed from the direction in which the face is viewed from the front is set to the front of the imaging unit 20.

FIG. 2 is a front view of the imaging unit 20. In the front view, the upper frame 64 and the arm 726 extend in the X-direction (the −X-direction described below) from the post 70. The upper frame 64 and the arm 726 do not necessarily extend only in the X-direction. Alternatively, for example, the upper frame 64 and the arm 726 can once extend in the Y-direction (the −Y-direction described below) and extend in the X-direction on the way.

A + side and a − side in each axial direction will be described below. The direction from the head MH toward the base 7B, namely, a lower side is set to a −Z-side, and the direction away from the base 7B, namely, an upper side is set to a +Z-side. In the shaft 66, the side supported by the upper frame 64 is the +Z-side, and the side supporting the turning arm 62 is the −Z-side. The direction in front of the head MH is set to a +Y-side, and the direction at the back of the head MH is set to a −Y-side. A right direction of the head MH is set to a +X-side, and a left direction is set to a −X-side. Each axial direction, each +, and each − are illustrated in a head perspective view MHPI that is a perspective view of the head MH in FIG. 1.

In the present application, a visual line direction is defined as follows. In each axial direction, the direction viewed in ascending order of a numerical value is viewed as a + direction view, and the direction viewed in descending order of the numerical value is set to a − direction view. Specifically, +ZV illustrated in the head perspective view MHPI is a +Z-direction view, −ZV is a −Z-direction view, +YV is a +Y-direction view and −YV is a −Y-direction view, +XV is a +X-direction view, and −XV is a −X-direction view.

An xyz-orthogonal coordinate system is an orthogonal coordinate system defined in the turning arm 62 that rotates with respect to a portion (for example, the post 70) fixed in the imaging unit 20. At this point, the axial direction of the shaft 66 is set to a z-axis direction, and the z-axis direction is matched with the Z-axis direction of an XYZ-orthogonal coordinate system. A direction in which the X-ray generator 42 and the X-ray detector 52 are opposed to each other is set to a y-axis direction, and a direction orthogonal to the y-axis direction and the z-axis direction is set to an x-axis direction. The turning arm 62 rotates with the shaft 66 as a rotation axis, which allows the xyz-orthogonal coordinate system to rotate about the Z-axis (=z-axis) with respect to the XYZ-orthogonal coordinate system. In the present application, sometimes the z-axis direction is referred to as a z-direction, the y-axis direction is referred to as a y-direction, and the x-axis direction is referred to as an x-direction.

In the y-axis direction, the side of the X-ray detector 52 as viewed from the X-ray generator 42 is set to a +y-side. In the x-axis direction, the right side toward the +y-side is set to a +x-side. The upper side in the vertical direction in the z-axis direction is set to a +z-side. Similar to the XYZ-orthogonal coordinate system, in each axial direction, the direction viewed in ascending order of the numerical value is referred to as the + direction view, and the direction viewed in descending order of the numerical value is referred to as the − direction view.

The X-ray tomography apparatus 10 includes the imaging unit 20 and an information processor 30.

<Imaging Unit 20>

The imaging unit 20 is an apparatus that collects X-ray projection data by performing X-ray imaging of the subject M1. The imaging unit 20 includes an X-ray generation unit 40, an X-ray detection unit 50, the support 60, the post 70, and an imaging controller 80.

<X-Ray Generator 40>

The X-ray generation unit 40 includes the X-ray generator 42 and an X-ray regulating unit 44.

The X-ray generator 42 includes an X-ray tube that is an X-ray source that emits an X-ray. Intensity (output intensity) of an X-ray beam emitted from the X-ray generator 42 can be controlled by changing voltage and/or current supplied to the X-ray tube. Operation of the X-ray generator 42 is controlled by an X-ray generation controller 810 of the imaging controller 80.

The X-ray regulating unit 44 regulates spread of the X-ray beam emitted from the X-ray generator 42, and forms the X-ray beam having a shape according to an imaging purpose. That is, the X-ray regulating unit 44 controls an X-ray irradiation range with respect to the subject M1 (examinee). The operation of the X-ray regulating unit 44 is controlled by the X-ray generation controller 810.

For example, the X-ray regulating unit 44 includes an X-ray shielding member disposed at a position close to the X-ray generator 42 and a moving mechanism (not illustrated) that moves the X-ray shielding member. For example, the X-ray shielding member is constructed with a single plate member in which a plurality of openings having different opening shapes are provided or at least two plate members in which an opening having a required size or shape is formed by moving the plate members in an approaching or separating direction. For example, the moving mechanism is constructed with a ball screw mechanism or a linear motor mechanism.

The X-ray generator 42 and the X-ray regulating unit 44 are accommodated in a casing 46. The casing 46 is supported by the support 60 (in this case, the turning arm 62).

<X-Ray Detection Unit 50>

The X-ray detection unit 50 includes the X-ray detector 52. The X-ray detector 52 detects the X-ray beam emitted from the X-ray generator 42. The X-ray detector 52 includes a flat panel detector (FPD) including a detection surface spreading two-dimensionally or an X-ray image intensifier (I.I.).

The X-ray detector 52 is attached to a side portion of a casing 54 facing the X-ray generator 42, and the X-ray beam is emitted from the X-ray generator 42 to a detection surface of the X-ray detector 52. The casing 54 supporting the X-ray detector 52 is supported by the support 60 (in this case, the turning arm 62).

<Support 60>

The support 60 includes the turning arm 62 and the upper frame 64. The turning arm 62 is suspended from the upper frame 64 via the shaft 66. The casing 46 is attached to one end of the turning arm 62, and the casing 54 is attached to the other end of the turning arm 62. That is, the turning arm 62 supports the X-ray generator 42 at one end side with the casing 46 interposed therebetween, and supports the X-ray detector 52 at the other end side with the casing 54 interposed therebetween.

The insides of the casings 46, 54 and the turning arm 62 form a series of cavities. Wirings (such as a signal wiring, a power supply wiring, and a control wiring) that operate each elements of the X-ray generation unit 40 and the X-ray detection unit 50 are disposed in the cavities. A working opening used to attach the wiring and a control board or an opening used to radiate heat can be provided at appropriate positions of the casings 46, 54 and the turning arm 62.

As illustrated in FIG. 2, the upper frame 64 is attached to the post 70. The shaft 66 extending in the Z-axis direction is attached to the upper frame 64, and the end of the shaft 66 is connected to an intermediate position between portions supporting the X-ray generation unit 40 and the X-ray detection unit 50 in the turning arm 62. Consequently, the turning arm 62 is suspended from the upper frame 64 via the shaft 66.

A turning drive unit 642 is provided in the upper frame 64. The turning drive unit 642 rotates the shaft 66 to turn the turning arm 62 about the shaft 66. Although not illustrated, for example, the turning drive unit 642 includes an endless belt entrained about the shaft 66 and a motor that rotates the endless belt. The turning drive unit 642 can be provided in the turning arm 62. In this case, the turning arm 62 rotates relative to the non-rotating shaft 66. The operation of the turning drive unit 642 is controlled by a turning controller.

A turning axis 66A, which is an axis on which the turning arm 62 turns mechanically, is set in the shaft 66 in design. The turning arm 62, the casing 46, and the casing 54 constitute a turning unit 67. The upper frame 64 is a turning support 64A that supports the turning unit 67 via the shaft 66. The turning arm 62 turns about the axis of the shaft 66, whereby the turning unit 67 turns about the turning axis 66A.

The turning arm 62 supports the casing 46 at one end side, and supports the casing 54 at the other end side. Consequently, a part of the turning arm 62 supports the X-ray generator 42 while another part supports the X-ray detector 52, the turning axis 66A being sandwiched between the parts. That is, the support 60 supports the X-ray generator 42 and the X-ray detector 52.

An XY-direction movement drive unit 644 that moves the shaft 66 in the X-axis direction and the Y-axis direction is provided in the upper frame 64. For example, the XY-direction movement drive unit 644 is constructed with an XY-stage.

The XY-direction movement drive unit 644 moves the turning drive unit 642 in the X-axis direction and the Y-axis direction together with the shaft 66. For this reason, the shaft 66 is movable in the XY-plane, and is rotatable about the axis in the Z-axis direction at a specific position after the movement in the XY-plane.

The XY-direction movement drive unit 644 can be provided in the turning arm 62. In this case, the turning arm 62 moves in the X-axis direction and the Y-axis direction relative to the shaft 66 fixed at a constant position in the XY-plane.

Both of the turning drive unit 642 and the XY-direction movement drive unit 644 can be provided in the turning arm 62. In this case, the turning arm 62 moves relatively in the X-axis direction and the Y-axis direction and rotates relatively with respect to the shaft 66, which is fixed at the constant position in the XY-plane and does not rotate.

A Z-direction drive unit 646 that elevates and lowers the upper frame 64 in the Z-axis direction is provided in the upper frame 64 and the post 70. As illustrated in FIG. 2, the Z-direction drive unit 646 includes a motor 6462, a ball screw 6464, a nut 6466, and a plurality (in this case, four) of rollers 6468.

The motor 6462 rotates the ball screw 6464. The ball screw 6464 extends in the Z-axis direction. The nut 6466 is screwed in the ball screw 6464.

Each of the rollers 6468 is engaged with a pair of rails 702 provided on the post 70, and the movement direction of the roller 6468 is restricted such that the roller 6468 moves only in the extending direction (Z-axis direction) of the pair of rails 702.

In the example of FIG. 2, the motor 6462 is attached to the post 70, and the nut 6466 is fixed to the upper frame 64. Each roller 6468 is attached to the upper frame 64.

The motor 6462 rotates the ball screw 6464 clockwise or counterclockwise, whereby the nut 6466 moves upward or downward along the ball screw 6464. At this point, the rollers 6468 move on the pair of rails 702. Consequently, the upper frame 64 is elevated or lowered in the Z-axis direction. The X-ray generation unit 40 and the X-ray detection unit 50, which are supported by the turning arm 62, move in the Z-axis direction in association with the elevating and lowering movement of the upper frame 64.

<Post 70>

The post 70 is a member extending in the Z-axis direction, and supports the upper frame 64 and the subject holder 72.

<Subject Holder 72>

The subject holder 72 is a member that holds the subject M1. In this example, the subject holder 72 includes the chin rest 722, a lower frame 724, the arm 726, and an elevation drive unit 728.

The chin rest 722 supports a jaw of the subject M1 to support the head of the subject M1. The subject holder 72 is connected to the lower frame 724 via the arm 726. The subject holder 72 can include a member (an ear rod or an arm sandwiching the left and right of the head of the subject M1) such as an ear rod that fixes the head of the subject M1 from both sides. A mechanical element, which is constructed with the chin rest 722 and the ear rod to fix the head MH of the subject M1, constitutes the subject holder 72 or a part of the subject holder 72 as a head support 72H.

The lower frame 724 is attached to the post 70, and moves in the Z-axis direction. The lower frame 724 moves in the Z-axis direction, whereby the chin rest 722 fixed to the arm 726 moves in the Z-axis direction.

The arm 726 is a member that connects the lower frame 724 and the chin rest 722. In the example of FIG. 2, the arm 726 is constructed with a portion extending in parallel to the XY-plane from the lower frame 724 and a portion, which extends to the Z-axis and is connected to the chin rest 722.

The elevation drive unit 728 includes a motor 7282, a ball screw 7284, a nut 7286, and a plurality of (four in this case) rollers 7288.

The motor 7282 rotates the ball screw 7284. The ball screw 7284 extends in the Z-axis direction. The nut 7286 is screwed in the ball screw 7284.

Each of the rollers 7288 is engaged with the pair of rails 702, and the moving direction of the roller 7288 is restricted so as to move only in the extending direction (Z-axis direction) of the pair of rails 702. In the example of FIG. 2, the motor 7282 and the ball screw 7284 are fixed to the lower frame 724. The nut 7286 is fixed to the upper frame 64. In the illustrated example, the ball screw 7284 extends in the +Z direction from a top of the lower frame 724, and is screwed in the nut 7286 fixed in the vicinity of the bottom of the upper frame 64. Each of the rollers 7288 is attached to the lower frame 724.

When the motor 7282 rotates the ball screw 7284 clockwise or counterclockwise, the lower frame 724 moves upward or downward with respect to the nut 7286 fixed to the upper frame 64. At this point, each of the rollers 7288 moves along the pair of rails 702, whereby the lower frame 724 moves in the Z-axis direction.

The lower frame 724 moves in the Z-axis direction, whereby the chin rest 722 moves along the Z-axis. The support 60 is elevated or lowered together with the subject holder 72 to be matched with the position of the head MH of the subject M1 by the Z-direction drive unit 646, the head MH is fixed to the head support 72H, and the elevation drive unit 728 lowers the subject holder 72 by the same drive amount as the support 60 at the same time as the Z-direction drive unit 646 elevates the support 60, or the elevation drive unit 728 elevates the subject holder 72 by the same drive amount as the support 60 at the same time as the Z-direction drive unit 646 lowers the support 60. Consequently, the support 60 is elevated or lowered with respect to the head MH by the relative movement while a height of the head MH is kept constant, which allows the X-ray irradiation location to be changed in the Z-axis direction.

The position where the head of the subject M1 is supported can be changed by changing the position in the Z-axis direction of the chin rest 722. For example, the position of the chin rest 722 is set according to the position of the head of the subject M1 in an upright posture.

<Imaging Controller 80>

The imaging controller 80 controls the operation of each element of the imaging unit 20 to cause the imaging unit 20 to perform the X-ray imaging. A hardware configuration of the imaging controller 80 is similar to that of a general computer or a work station. That is, the imaging controller 80 includes a CPU that performs various arithmetic processing, a ROM that is a read-only memory in which a basic program is stored, a RAM that is a readable and writable memory in which various pieces of information are stored, and a storage in which a control application or data is stored.

The imaging controller 80 includes a turning controller 802, an XY-direction movement controller 804, a Z-direction movement controller 806, an X-ray detection controller 808, and an X-ray generation controller 810. Each controller is a function implemented by the operation of the CPU (general-purpose circuit) according to the controlling application. A part or all of the functions can be implemented in a hardware manner by construction of a dedicated circuit. Among the circuits of the CPU, portions used for various kinds of control by various control applications can be grasped as the controllers 802, 804, 806, 808, and integration thereof can be grasped as the imaging controller 80.

The turning controller 802 controls the turning of the turning arm 62 by controlling the operation of the turning drive unit 642. Specifically, the turning controller 802 changes an irradiation angle of an X-ray beam BX1 with respect to the subject M1 by rotating the X-ray generator 42 supported by the turning arm 62 around the shaft 66.

By controlling the operation of the XY-direction movement drive unit 644, the XY-direction movement controller 804 controls the movement of the turning arm 62 in the X- and Y-axis directions as a result of the movement of the shaft 66 in the X-axis direction and the Y-axis direction. Specifically, the XY-direction movement controller 804 moves the X-ray generator 42 and the X-ray detector 52 in the X-axis direction and the Y-axis direction.

The turning drive unit 642 and the XY-direction movement drive unit 644 constitute a turning movement drive unit 64D, and the turning controller 802 and the XY-direction movement controller 804 constitute a turning movement drive controller 80D.

The Z-direction movement controller 806 controls the movement of the turning arm 62 in the Z-direction by controlling the operation of the Z-direction drive unit 646. Specifically, the Z-direction movement controller 806 moves the X-ray generator 42 and the X-ray detector 52 in the Z-direction.

The X-ray detection controller 808 controls the operation of the X-ray detection unit 50. The X-ray detection controller 808 controls the operation of the X-ray detector 52.

The X-ray generation controller 810 controls the operation of the X-ray generation unit 40. For example, the X-ray generation controller 810 controls the operation of the X-ray generator 42. Specifically, on and off of the X-ray beam emitted from the X-ray generator 42 and the intensity of the X-ray beam are controlled by controlling the voltage or current supplied to the X-ray tube. The X-ray generation controller 810 controls shielding of the X-ray beam by controlling the operation of the X-ray regulating unit 44. The X-ray beam (such as an X-ray narrow beam and an X-ray cone beam) having the shape according to the imaging purpose is formed by the shielding control of the X-ray beam. The X-ray generation controller 810 controls the operation of the X-ray regulating unit 44 to prevent the region other than an imaging region ROI in the subject M1 from being irradiated with the X-ray beam.

A display 82 and an operation panel 84 are connected to the imaging controller 80. The display 82 is constructed with a liquid crystal display or the like, and provided to display various pieces of information. The operation panel 84 is configured of a touch panel display, and is provided for an operator to input various pieces of information (including an imaging condition) to the imaging controller 80.

<Information Processor 30>

A hardware configuration of the information processor 30 is similar to that of a general computer or a work station. That is, the information processor 30 includes a CPU that performs various pieces of arithmetic processing, a ROM that is a read-only memory in which a basic program is stored, a RAM that is a readable and writable memory in which various pieces of information are stored, and a storage 31 in which an application or data is stored.

The information processor 30 includes an imaging region setting unit 302, a tomographic layer-of-interest setting unit 304, an imaging trajectory setting unit 306, and an image processor 308. Each processor is a function implemented by the operation of the CPU according to the application. However, some or all of these functions can be realized in hardware by a dedicated circuit. Among the circuits of the CPU, portions used for various kinds of control by various control applications can be grasped as the setting units 302, 304, 306, 308, and integration thereof can be grasped as the information processor 30.

<Imaging Region Setting Unit 302>

The imaging region setting unit 302 has a function of setting the imaging region ROI. The imaging region ROI is a region that, when the imaging unit 20 performs the X-ray imaging, is irradiated with the X-ray beam from a plurality of directions to acquire a plurality of X-ray projection images. The imaging region setting unit 302 sets the imaging region ROI based on an input operation input by the operator through the operation unit 34. A virtual space on arithmetic operation corresponding to a real space of the imaging unit 20 is defined in the information processor 30. The setting of the imaging region ROI means the setting of a position, a size, a shape, and the like of the imaging region ROI in the virtual space defined in the information processor 30. A specific method for setting the imaging region ROI will be described later.

<Tomographic Layer-of-Interest Setting Unit 304>

The tomographic layer-of-interest setting unit 304 has a function of setting a tomographic layer of interest LOI. The tomographic layer of interest LOI is usually a tomographic layer on which the operator wants to perform the imaging. The tomographic layer-of-interest setting unit 304 sets the tomographic layer of interest LOI based on the information input to the information processor 30 by the operator through the operation unit 34. "The setting of the tomographic layer of interest LOT" means the setting of the tomographic layer of interest LOI in the virtual space defined by the information processor 30. For example, the tomographic layer of interest LOI is set by the following procedure.

As illustrated in FIG. 3, the tomographic layer-of-interest setting unit 304 determines the position, the size, and an orientation (normal direction DN1) of a tomographic plane of interest SL1 based on the operation input of the operator. The tomographic layer-of-interest setting unit 304 sets the tomographic layer of interest LOI having a required thickness in the normal direction DN1 based on the tomographic plane of interest SL1. In the example of FIG. 3, the tomographic layer of interest LOI having a thickness TN1 in the normal direction DN1 is set around the tomographic plane of interest SL1. The thickness TN1 of the tomographic layer of interest LOI can be set based on designated input from the operator, or can be a predetermined specified value. When the thickness TN1 is the specified value, for example, the position of the tomographic layer of interest LOI, characteristics (such as a height, a weight, age, and gender) of the subject, or the specified value according to an imaging site is previously made into a database and stored in the storage 31, and called according to the imaging. The setting of the tomographic layer of interest LOI will be described later.

When the tomographic layer of interest LOI is set to a front teeth region, as illustrated in FIG. 3, the thickness direction of the thickness TN1 can be matched with the Y-direction, and a width direction of the width W1 can be matched with the X-direction. For other regions, vectors in the X-direction and the Y-direction can be adapted according to the region.

<Imaging Trajectory Setting Unit 306>

The imaging trajectory setting unit 306 has a function of setting trajectories (imaging trajectories) of the X-ray generator 42 and the X-ray detector 52 during the X-ray imaging when the imaging unit 20 performs the X-ray imaging. Specifically, in the imaging trajectory setting unit 306, a turning center axis RA1 parallel to the Z-axis passing through the center of the imaging region ROI is set to the rotation center, and a circular trajectory when the X-ray generator 42 and the X-ray detector 52 are rotated about the turning center axis RA1 at a predetermined rotation radius is set to a normal imaging trajectory. The imaging trajectory setting unit 306 changes the normal imaging trajectory according to the position of the tomographic layer of interest LOI set by the tomographic layer-of-interest setting unit 304. Specifically, the imaging trajectory setting unit 306 changes the normal imaging trajectory to determine the final imaging trajectory such that the X-ray generator 42 is moved away from the tomographic layer of interest LOI and the X-ray detector 52 approaches the tomographic layer of interest LOI when the X-ray generator 42 confronts the tomographic layer of interest LOI. The setting of the imaging trajectory will be described later.

<Image Processor 308>

The image processor 308 processes the X-ray projection image, which is generated based on the signal output by the X-ray detector 52 when the imaging unit 20 performs the X-ray imaging, and generates an X-ray tomographic image of the tomographic layer of interest LOI. The image generated by the image processor 308 is not limited to the X-ray tomographic image of the tomographic layer of interest LOI. For example, after the X-ray imaging, the operator can receive designation of another tomographic layer in the imaging region ROI, and the image processor 308 can generate the X-ray tomographic image corresponding to the tomographic layer.

The display 32 and the operation unit 34 are connected to the information processor 30.

The display 32 is constructed with a liquid crystal display or the like, and provided to display various pieces of information. Specifically, the display 32 displays a display image with which the operator designates a condition of the X-ray imaging, a display image with which the operator designated the imaging region ROI or the tomographic layer of interest LOI, and the X-ray tomographic image generated by the image processor 308.

The operation unit 34 is constructed with various input devices such as a keyboard and a mouse. As an example, the operation unit 34 is operated when the operator designates the imaging region ROI. That is, the operation unit 34 is an example of an imaging region designation unit. The display 32 can have a part or all of the functions of the operation unit 34 by constructing the display 32 with a touch panel. The imaging region ROI and the tomographic layer of interest LOI can be designated through the operation panel 84 connected to the imaging controller 80.

<Method for Setting Tomographic Layer of Interest LOI or Imaging Region ROI>

A method for setting the tomographic layer of interest LOI or the imaging region ROI will be described below with reference to FIGS. 4 to 8. In the following description, it is assumed that the tomographic layer of interest LOI or the imaging region ROI is set to the jaw in the head of the subject M1. However, the tomographic layer of interest LOI or the imaging region ROI is not limited to the case where the tomographic layer of interest LOI or the imaging region ROI is set to the jaw, and can be set to another site.

Figure 4:
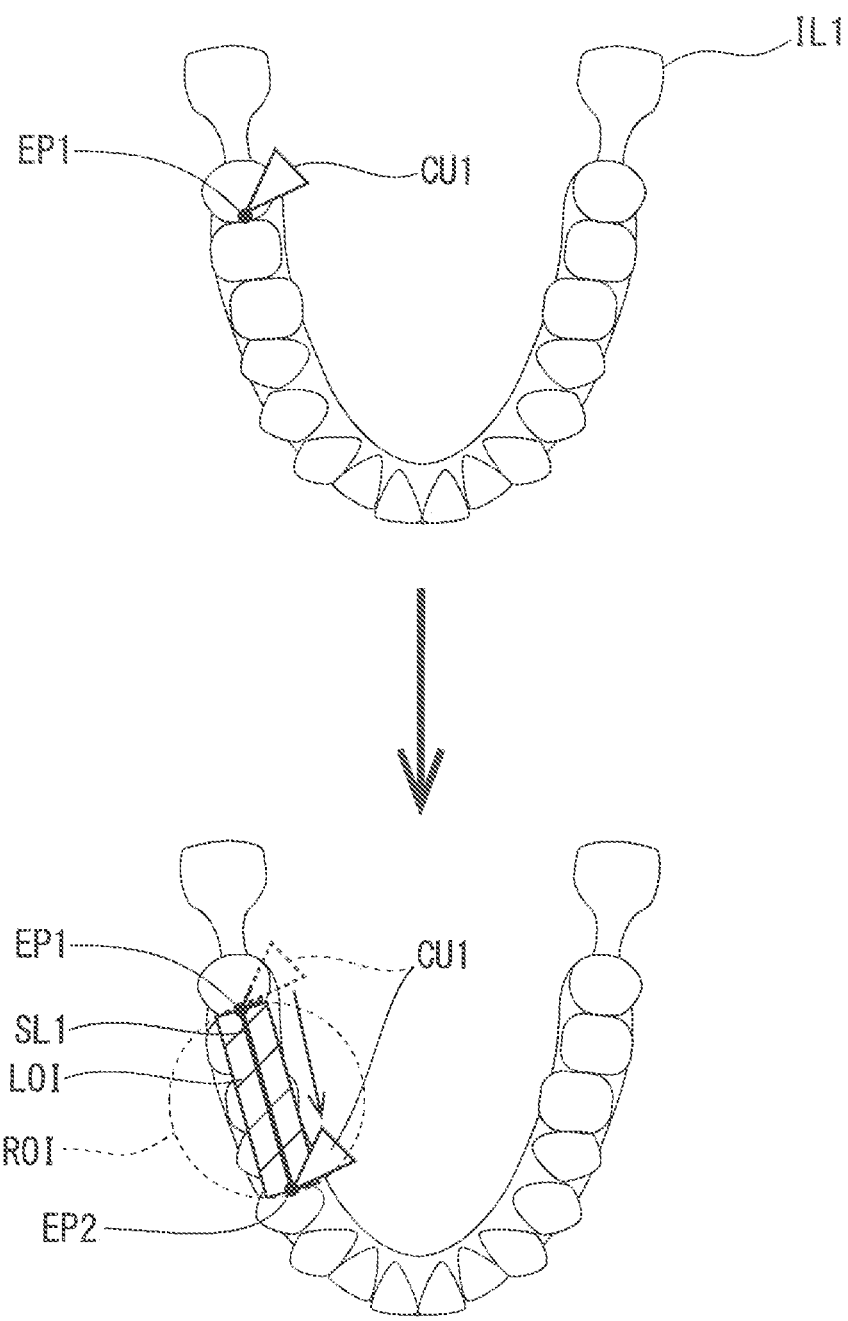
FIG. 4 is a view illustrating a method for setting the tomographic layer of interest LOI.

FIG. 4 is a view illustrating the method for setting the tomographic layer of interest LOI. In the setting method of FIG. 4, the display 32 displays a schematic diagram IL1 that simulates a lower jaw as a designation image for designating the tomographic layer of interest LOI. A plurality of teeth are also drawn in the schematic diagram ILL The operator designates two end points EP1, EP2 with respect to the schematic diagram IL1 displayed on the display 32 using a cursor (or mouse pointer) CU1. Specifically, when the operation unit 34 includes a mouse, the end points EP1, EP2 can be designated by moving the cursor (or mouse pointer) CU1 through a drag operation. The positions of the end points EP1, EP2 correspond to the positions of two points in the XY-plane in the real space.

The linear tomographic plane of interest SL1 having end points EP1, EP2 at both ends is set when the two end points EP1, EP2 are designated (see FIG. 3). In this case, the end points EP1, EP2 have a width W1 of the tomographic plane of interest SL1. However, the end points EP1, EP2 are not necessarily set to both ends. For example, the tomographic plane of interest SL1 having any width can be set on a straight line passing through the end points EP1, EP2.

When the tomographic plane of interest SL1 is set, the linear tomographic layer of interest LOI is set in the XY-plane having the required thickness TN1 in the normal direction DN1 based on the tomographic plane of interest SL1. In FIG. 4, although the tomographic layer of interest LOI is illustrated as a rectangle in planar view, a length (a vertical width W2 corresponding to the height when the LOI is viewed from the normal direction DN1 in FIG. 3) in a depth direction (corresponding to the Z-axis direction of the real space) of the tomographic layer of interest LOI) is also set appropriately. The vertical width W2 of the tomographic layer of interest LOI can be designated by the operator, or automatically determined according to the physical characteristics (such as the gender, the age, the height, and the weight) or the imaging site of the subject M1 by the tomographic layer-of-interest setting unit 304.

Figure 5:
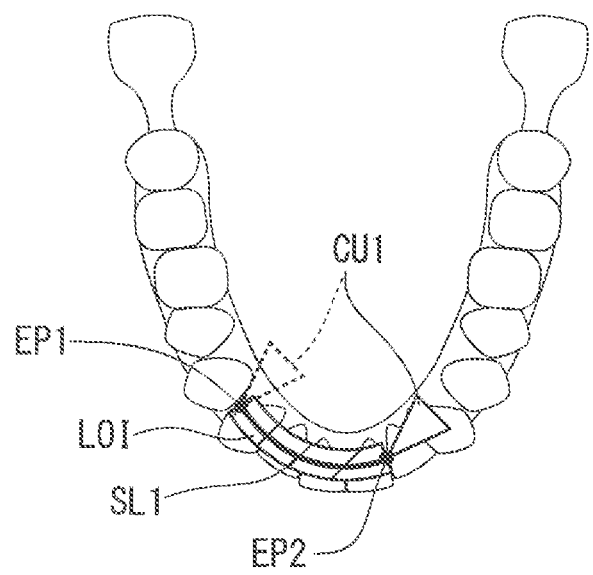
FIG. 5 is a view illustrating the method for setting the tomographic layer of interest LOI.

FIG. 5 is a view illustrating the method for setting the tomographic layer of interest LOI. In the setting method of FIG. 4, the tomographic layer of interest LOI is set to the shape extending linearly in the XY-plane. Alternatively, as illustrated in FIG. 5, the tomographic layer of interest LOI can be set to a curved shape. In this case, for example, when the operator performs a drag operation to move the cursor CU1 in a curved manner, the tomographic layer-of-interest setting unit 304 sets the tomographic plane of interest SL1 to the curved shape according to the movement trajectory of the cursor CU1. The tomographic layer-of-interest setting unit 304 can set the tomographic layer of interest LOI along the tomographic plane of interest extending in the curved manner based on the tomographic plane of interest SL1. When a plurality of points are designated by the cursor CU1, curve interpolation between them can automatically be performed.

Figure 6:
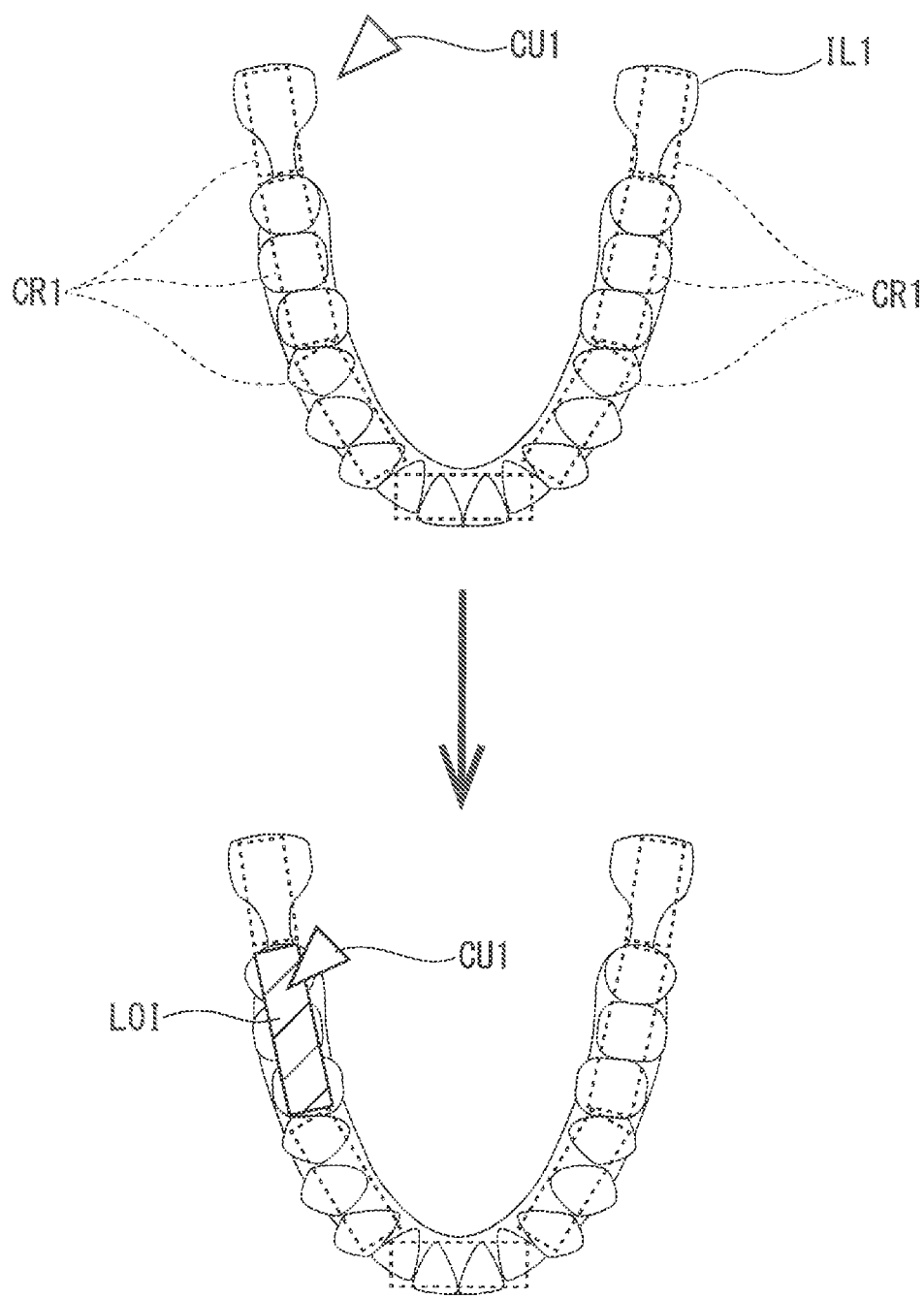
FIG. 6 is a view illustrating the method for setting the tomographic layer of interest LOI.

FIG. 6 is a view illustrating the method for setting the tomographic layer of interest LOI. In the setting methods of FIGS. 4 and 5, the operator sets the tomographic layer of interest LOI to any position. On the other hand, in the setting method of FIG. 6, a plurality of candidate regions that are candidates of the tomographic layer of interest LOI are previously specified, and the operator selects the tomographic layer of interest LOI from among these candidate regions. In the example of FIG. 6, seven candidate regions CR1 are previously determined in the schematic diagram IL1 of the jaw displayed on the display 32, and each candidate region CR1 is displayed by a broken line. When the operator moves the cursor CU1, and performs an operation to select the specific candidate region CR1 from among the plurality of candidate regions CR1, the tomographic layer-of-interest setting unit 304 sets the selected candidate region CR1 to the tomographic layer of interest LOI. In this case, although a degree of freedom in setting the tomographic layer of interest LOI is decreased, the designation operation of the tomographic layer of interest LOI can easily be performed.

Figure 7:
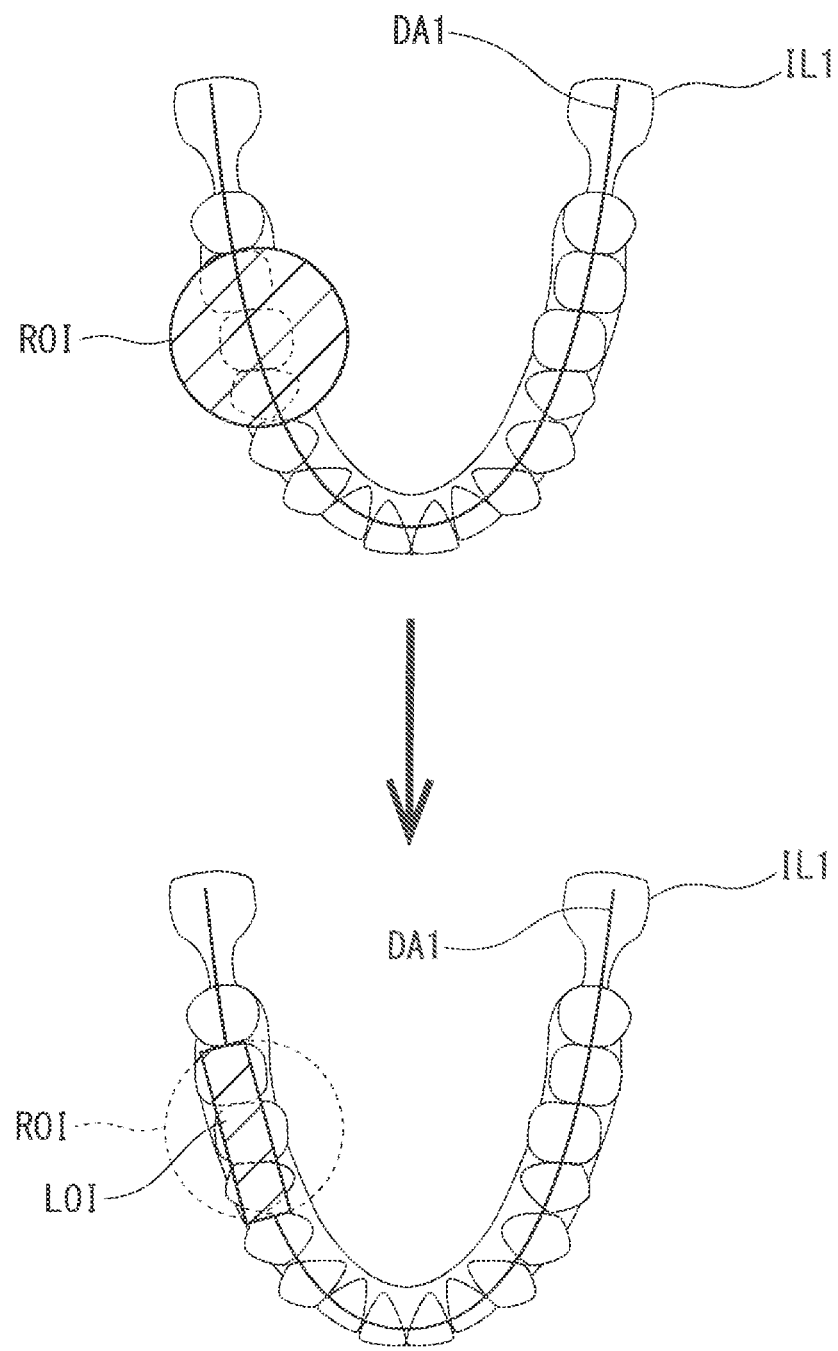
FIG. 7 is a view illustrating a method for setting an imaging region ROI and the tomographic layer of interest LOI.

FIG. 7 is a view illustrating the method for setting the imaging region ROI and the tomographic layer of interest LOI. In the setting method of FIGS. 4, 5, and 6, the operator directly designates the tomographic layer of interest LOI on the designation image. On the other hand, in the setting method of FIG. 7, after the imaging region setting unit 302 sets the imaging region ROI, the tomographic layer-of-interest setting unit 304 automatically sets the tomographic layer of interest LOI according to the imaging region ROI.

For example, the imaging region ROI can be set as follows. That is, the operator designates the position of the imaging region ROI (for example, the center position of the imaging region ROI) and the radius of the imaging region ROI using the cursor CU1 or the like. In response to the designation, the imaging region setting unit 302 sets the imaging region ROI having the designated radius at the designated position. The radius of the imaging region ROI can be designated by numerical input through the keyboard or the like, or designated by the drag operation using the mouse. Circular frames having various radii indicating the size of the imaging region ROI can previously be prepared, and the operator can select the frame having the specific radius from among the circular frames. In this case, the imaging region setting unit 302 can set the imaging region ROI at the position where the selected frame is disposed according to the disposition of the selected frame at the required position on the schematic diagram IL1.

Subsequently, the tomographic layer-of-interest setting unit 304 automatically sets the tomographic layer of interest LOI according to a predetermined rule for the set imaging region ROI. For example, when the imaging target is the jaw, the tomographic layer-of-interest setting unit 304 can set the tomographic layer of interest LOI based on a dental arch DA1 defined along the jaw. For example, as illustrated in FIG. 7, it is assumed that the dental arch DA1 curved into a U-shape is defined in the schematic diagram IL1 of the jaw, and that the imaging region ROI is set so as to include the dental arch DA1. In this case, the tomographic layer-of-interest setting unit 304 can automatically set the tomographic layer of interest LOI along a part of the dental arch DA1 included in the imaging region ROI.

When the linear tomographic layer of interest LOI is set from the curved dental arch DA1, for example, a point on the portion of the dental arch DA1 of the imaging region ROI is taken as a representative point, and the tomographic layer of interest LOI can be set on a tangential line on the representative point of the dental arch DA1. For example, when the shape of the imaging region ROI is a circle as viewed from the z-axis direction (+z-direction or −z-direction), one point on the portion can be set to the center of the circle of the imaging region ROI. The tomographic layer of interest LOI can be set on a line obtained by translating the tangential line in a buccolingual direction. For example, the tomographic layer of interest LOI can be set on a line that is slightly translated in a lingual direction so as to pass through substantially the entire center of the target teeth. Two points on a portion of the dental arch DA1 in the imaging region ROI can be selected, and the tomographic layer of interest LOI can be set on a straight line connecting the two points. The size of the imaging region ROI can be variable, and the size of the frame indicating the imaging region ROI can be changed by the drag operation using the mouse or the like. In this case, an X-ray restriction amount of the X-ray regulating unit 44 can be changed according to the change in the size of the imaging region ROI.

The shape of the imaging region ROI viewed in the z-direction does not need to be a perfect circle. The imaging region ROI can have an elliptical shape in which a major diameter is aligned with a row of teeth. In this case, the ROI three-dimensionally has an elliptical cylindrical shape. Preferably, the rotation center of the X-ray generator 42 and the X-ray detector 52 is placed at the center of the ellipse in accordance with the ROI having the elliptical cross-section, and the X-ray regulating unit 44 controls the spread of the X-ray beam. Specifically, the spread of the X-ray beam is narrowed when the center axis X-ray of the X-ray beam intersects a minor axis, and the spread of the X-ray beam is widened when the center axis X-ray of the X-ray beam intersects the major axis.

The curved tomographic layer of interest LOI of the tomographic layer-of-interest setting unit 304 can be set based on the curved dental arch DA1. For example, a curved portion of the dental arch DA1 in the imaging region ROI can be set to the tomographic plane of interest SL1, and a region having a predetermined thickness based on the curved portion can be set to the tomographic layer of interest LOI.

Figure 8:
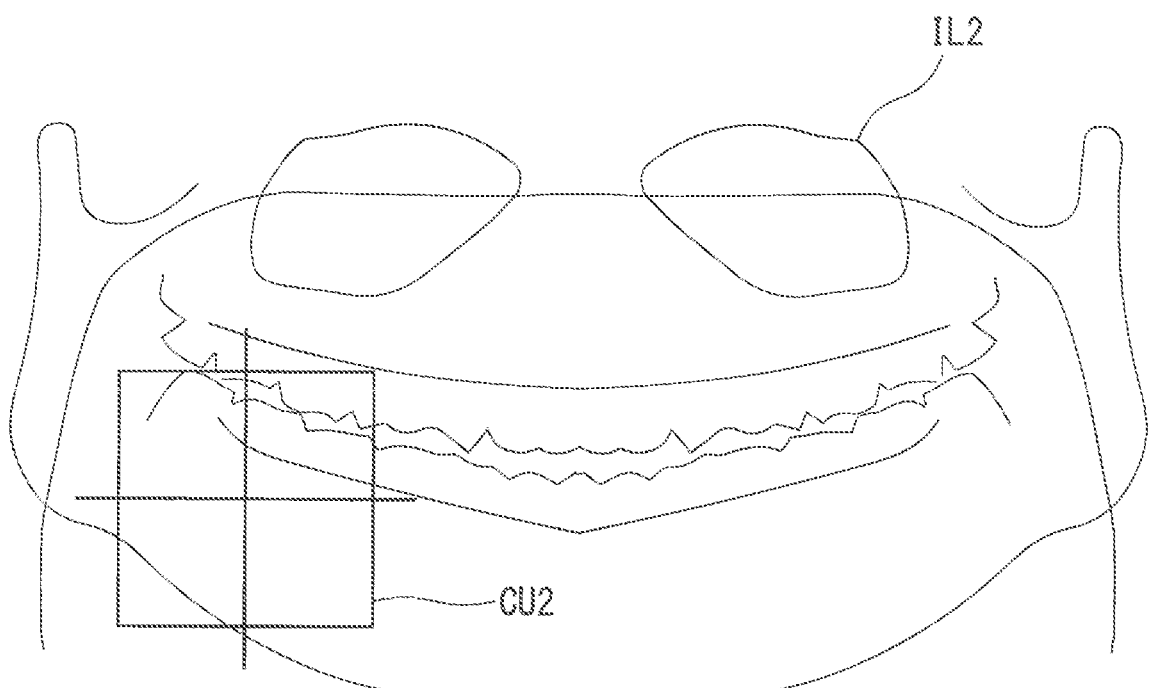
FIG. 8 is a view illustrating the method for setting the tomographic layer of interest LOI.

FIG. 8 is a view illustrating the method for setting the tomographic layer of interest LOI. In the setting method of FIG. 8, a panoramic X-ray image IL2 obtained by previously performing panoramic imaging of the jaw of the subject M1 is used as the designation image. The panoramic X-ray image IL2 is displayed on the display 32, and the tomographic layer of interest LOI or the imaging region ROI is set on the panoramic X-ray image IL2. Each pixel constituting the panoramic X-ray image IL2 has information about a coordinate position on the real space. For this reason, the coordinate position corresponding to the specific portion in the real space is specified when a specific portion on the panoramic X-ray image IL2 is selected using a cursor CU2. At this point, the cursor CU2 includes two straight lines orthogonal to each other. The operator aligns the intersection of the two straight lines with the site to be observed, namely, the tomographic layer of interest LOI, and performs the operation (such as a mouse click operation) to specify the position. When the position of the tomographic layer of interest LOI is designated, as illustrated in FIGS. 4 to 7, the tomographic layer-of-interest setting unit 304 appropriately sets the linear or curved tomographic layer of interest LOI.

The methods for setting the tomographic layer of interest LOI in FIGS. 4 to 8 is merely illustrative. The present invention is not limited to the methods in FIGS. 4 to 8, and the tomographic layer of interest LOI can be set by another method.

For example, a plurality of X-ray projection images (fluoroscopic images) obtained by irradiating the subject M1 with the X-ray beam BX1 from a plurality of directions can be used as the designation image for designating the imaging region ROI or the tomographic layer of interest LOI. For example, the coordinate position on the real space corresponding to the designated position can be specified by receiving the designation of the position of the imaging region ROI or the tomographic layer of interest LOI on two fluoroscopic images obtained by imaging the subject M1 from two directions. The technique described in Japanese Patent Application Laid-Open No. 2004-329293 can be used when the coordinate position in the real space is specified from the fluoroscopic images in the two directions.

After the tomographic layer-of-interest setting unit 304 sets the tomographic layer of interest LOI, the imaging region setting unit 302 can set the imaging region ROI according to the tomographic layer of interest LOI. At this point, the imaging region ROI can be set such that the imaging region setting unit 302 includes the previously-set tomographic layer of interest LOI.

<Imaging Trajectory that Decreases Projection Magnification Factor>

Figure 9:
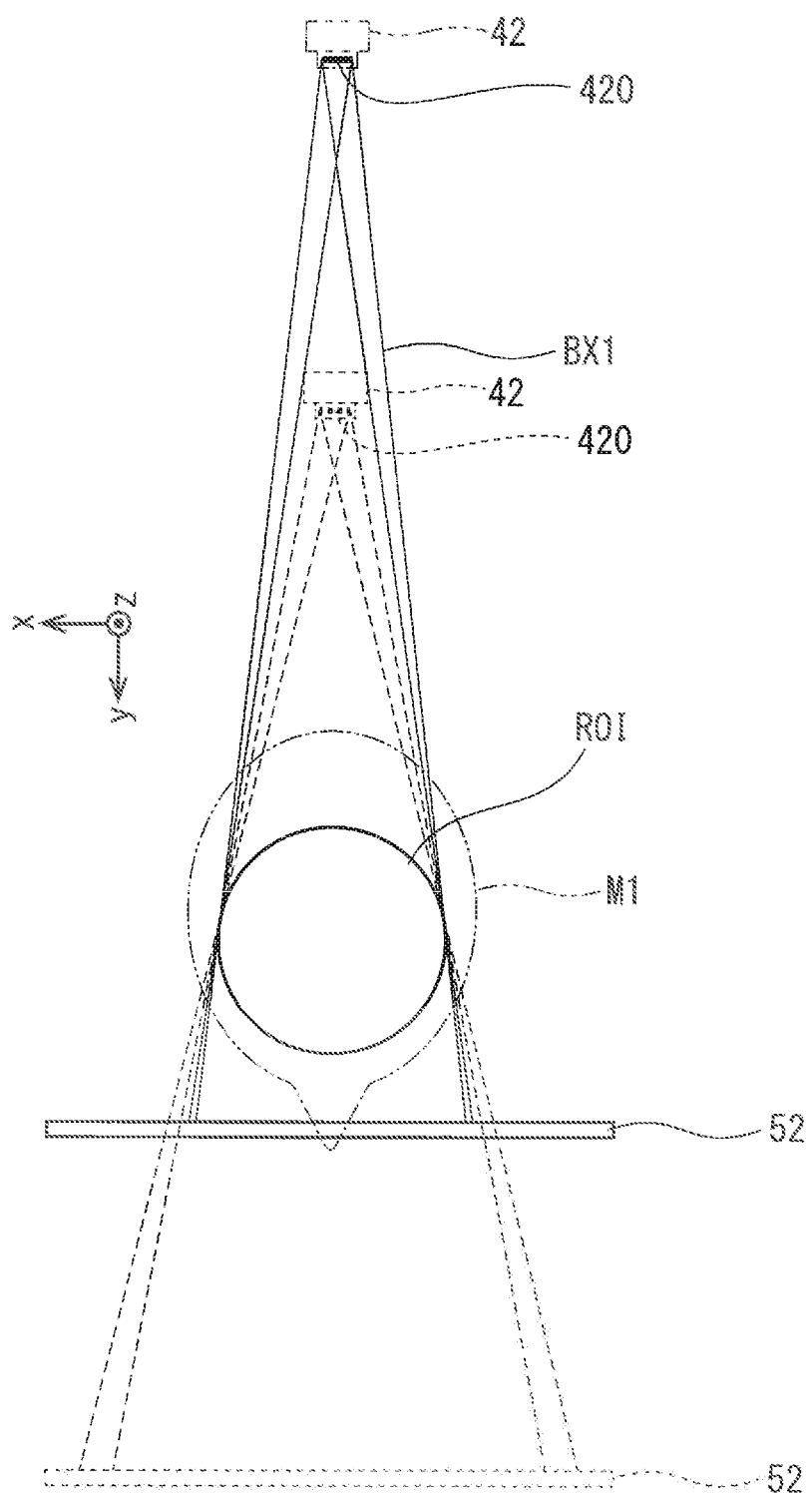
FIG. 9 is a view illustrating a relationship between a magnification factor and resolution in an X-ray projection image.

FIG. 9 is a view illustrating a relationship between a magnification factor and resolution in the X-ray projection image. FIG. 9 is a plan view schematically illustrating the X-ray generator 42 and the X-ray detector 52 when viewed from the +Z-side (in −Z-direction view). As illustrated in FIG. 9, the X-ray beam BX1 spreading in a fan shape is emitted from the X-ray tube of the X-ray generator 42. For this reason, the imaging region ROI is enlarged and projected onto the X-ray detector 52. Because the imaging region ROI is transmitted through the X-ray beam BX1, the magnification factor of the X-ray projection image (hereinafter, referred to as a "projection magnification factor") projected onto the X-ray detector 52 is determined by a distance from the X-ray generator 42 to the imaging region ROI and a distance from the imaging region ROI to the X-ray detector 52. In FIG. 9, when the X-ray generator 42 and the X-ray detector 52 move from the position indicated by the broken line to the position indicated by the solid line, the X-ray generator 42 moves away from the imaging region ROI, and the X-ray detector 52 approaches the imaging region ROI. This decreases the projection magnification factor. The X-ray detector 52 indicated by the solid line is drawn so as to overlap the nose of the subject M1. This is because the X-ray detector 52 is emphasized for the purpose of explanation of an approach and movement away principle.

In the X-ray detector 52, many X-ray detection elements are arrayed in the detection surface. Thus, the resolving power of the X-ray detector 52 is fixed, so that the resolution of the X-ray projection image can be improved by increasing the projection magnification factor. However, a focal point of the X-ray beam BX1 emitted from the X-ray generator 42 is not a point strictly, but a focal plane 420 having a certain size. An anode (focal plane 420) of the actual X-ray tube is inclined with respect to an X-ray irradiation axis. However, for convenience of illustration, in order to indicate that the focal plane 420 is not a point in principle, the anode is illustrated so as to be perpendicular to the X-ray irradiation axis. When attention is paid to a specific point of the imaging region ROI, an X-ray flux passing through the specific point in the X-ray beam BX1 emitted from the focal plane 420 is projected onto the detection surface of the X-ray detector 52 with constant spread. That is, the X-ray beam BX1 emitted from the focal plane 420 causes blurring on the X-ray projection image. When the projection magnification factor increases, a degree of blurring also increases, and resultantly the resolution (sharpness) of the X-ray projection image decreases.

Thus, in order to improve the resolution of the X-ray projection image, the projection magnification factor is desirably decreased as much as possible. For this reason, during the X-ray imaging, desirably, the X-ray detector 52 is caused to approach the imaging region ROI as much as possible, or the X-ray generator 42 is moved away from the imaging region ROI as much as possible.

However, when the X-ray detector 52 is caused to approach the imaging region ROI, the X-ray detector 52 can come into contact with the subject M1. When the X-ray generator 42 is moved away from the imaging region ROI, there is a possibility that the X-ray generation unit 40 accommodating the X-ray generator 42 collides with another member (for example, the post 70) of the imaging unit 20 or another member other than the imaging unit 20 disposed in the periphery.

The imaging trajectory setting unit 306 sets the imaging trajectory so as to decrease the projection magnification factor as much as possible while preventing the X-ray detector 52 from contacting with the subject M1 and preventing the X-ray generation unit 40 of the X-ray generator 42 from colliding with another member during the X-ray imaging. A specific method for setting the imaging trajectory will be described below.

Figure 10:
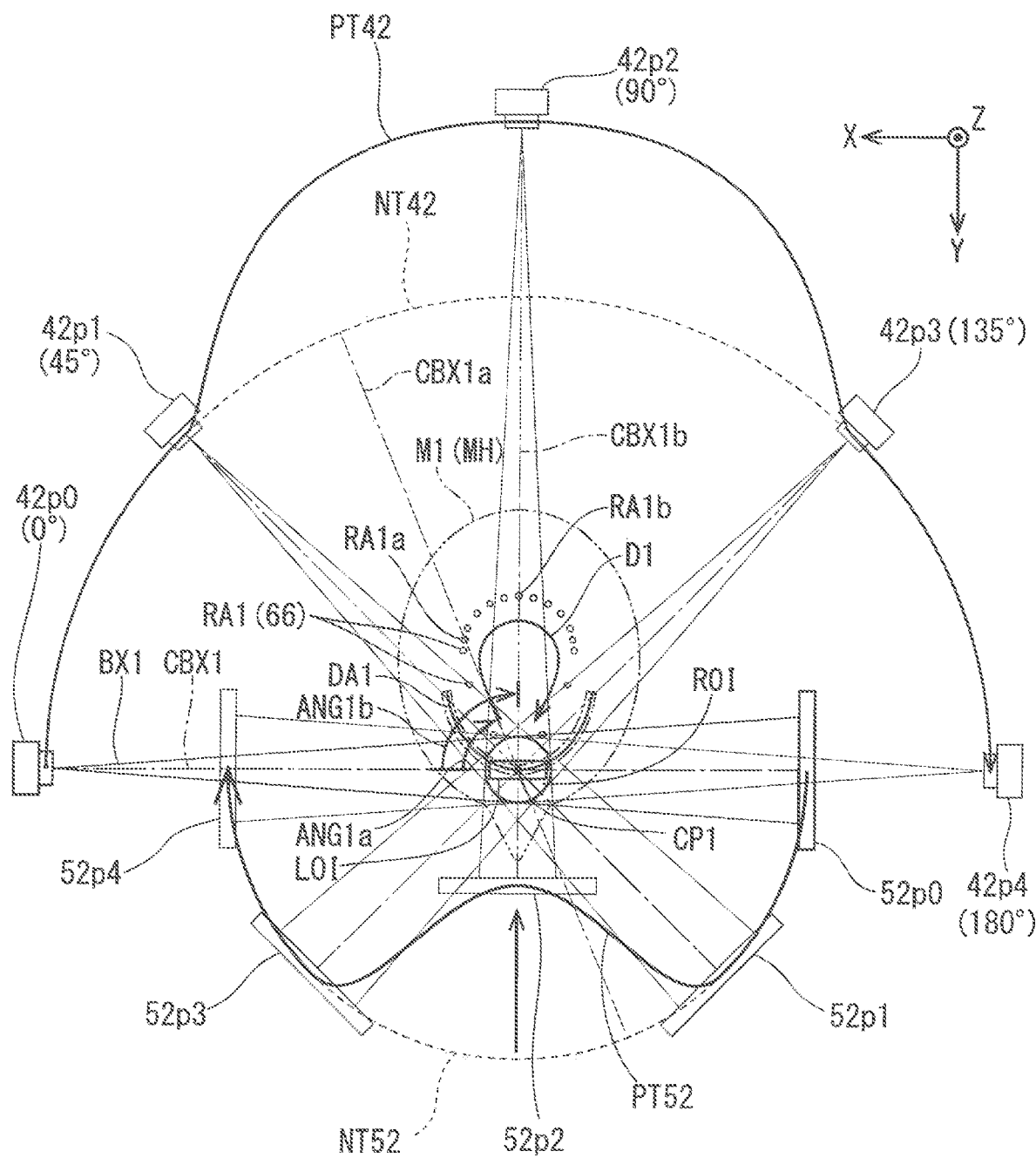
FIG. 10 is a view illustrating an example of X-ray imaging.

FIG. 10 is a view illustrating an example of the X-ray imaging. The X-ray imaging in FIG. 10 is CT imaging in which the X-ray generator 42 and the X-ray detector 52 are turned by 180° around the jaw of the subject M1. At this point, the vicinity of the front teeth of the subject M1 is set to the imaging region ROI, and the tomographic layer of interest LOI is set to a linear region along the dental arch DA1.

In the CT imaging, the X-ray generator 42 is turned by 180° from a position 42p0 on the right side of the head of the subject M1 to a position 42p4 on the left side of the head after passing through a rear side of the head. The X-ray detector 52 passes through a front side of the head from a position 52p0 on the left side of the head of the subject M1, and is turned by 180° to a position 52p4 on the right side of the head.

In the normal CT imaging, each of the X-ray generator 42 and the X-ray detector 52 is rotated at a constant rotation radius around a center point CP1 of the imaging region ROI. That is, the X-ray generator 42 and the X-ray detector 52 can be moved on normal imaging trajectories NT42, NT52. The X-ray generator 42 follows the normal imaging trajectory NT42, and the X-ray detector 52 follows the normal imaging trajectory NT52.

On the other hand, in the embodiment, the imaging trajectory setting unit 306 sets imaging trajectories PT42, PT52 in which, when the imaging trajectory setting unit 306 confronts the tomographic layer of interest LOI in the imaging region ROI, the projection magnification factor is smaller than that of non-confrontation. More specifically, when the X-ray generator 42 confronts the tomographic layer of interest LOI, as compared with the non-confrontation, the X-ray generator 42 is moved farther away from the tomographic layer of interest LOI, and the X-ray detector 52 is caused to approach the tomographic layer of interest LOI. The imaging trajectories PT42, PT52 are referred to as a magnification factor adjustment imaging trajectory, the X-ray generator 42 follows the magnification factor adjustment imaging trajectory PT42, and the X-ray detector 52 follows the magnification factor adjustment imaging trajectory PT52. The CT imaging with the magnification factor adjustment imaging trajectories PT42, PT52 is referred to as magnification factor adjustment CT imaging.

Figure 11:
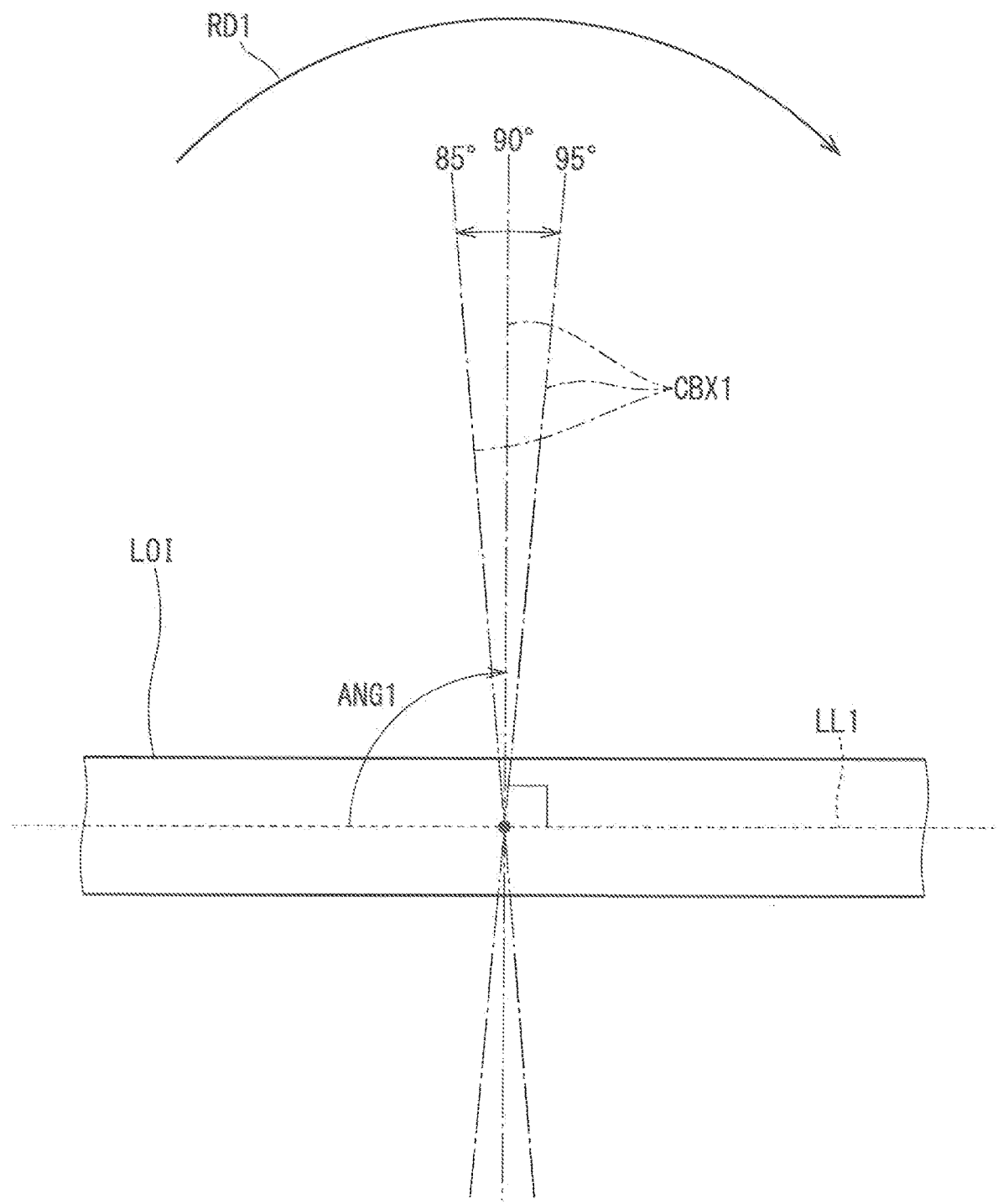
FIG. 11 is a view illustrating a center axis X-ray CBX1 incident on the tomographic layer of interest LOI.

FIG. 11 is a view illustrating a center axis X-ray CBX1 incident on the tomographic layer of interest LOI. Among the X-ray beams BX1, the X-ray passing through the turning center axis RA1 is set to the center axis X-ray CBX1. The center axis X-ray CBX1 is the X-ray matched with the irradiation axis of the X-ray beam BX1. The confrontation of the X-ray generator 42 with the tomographic layer of interest LOI (in other words, the irradiation axis of the X-ray beam BX1 is incident on the tomographic layer of interest LOI in a confronting manner) means a state in which the center axis X-ray CBX1 is incident on the tomographic layer of interest LOI at substantially right angles. The term "incident at substantially right angles" means the state in which an incident angle ANG1 of the center axis X-ray CBX1 with respect to the tomographic layer of interest LOI is in a range from 85° to 95°, and in particular, the state in which the center axis X-ray CBX1 is incident at right angles means the state in which the incident angle ANG1 becomes 90°.

The incident angle ANG1 means an angle around a turning direction RD1 from a center line LL1 to the center axis X-ray CBX1 when the center line LL1 passing through the center of the tomographic layer of interest LOI is defined as viewed from the upper side in the Z-axis direction, namely, in Z-direction view. In the CT imaging of FIG. 10, the X-ray generator 42 rotates clockwise with respect to the subject M1 as viewed from the +Z-side, that is, in −Z-direction view. For this reason, the incident angle ANG1 is a clockwise angle from the center line LL1 to the center axis X-ray CBX1. When the tomographic layer of interest LOI is formed into a shape extending in a curved line, the tangential line on the tomographic layer of interest LOI and at any point (for example, a barycentric point of the curve) on the curve along the tomographic layer of interest LOI is set to the center line LL1, and the angle between the center axis X-ray CBX1 and the center line LL1 is set to the incident angle ANG1.

In the CT imaging of FIG. 10, on the magnification factor adjustment imaging trajectory PT42, each of the positions 42p0 to 42p4 of the X-ray generator 42 is the position of the X-ray generator 42 where the incident angle ANG1 becomes 0°, 45°, 90°, 135°, and 180°. That is, the state in which the X-ray generator 42 confronts the tomographic layer of interest LOI (the state in which the irradiation axis of the X-ray beam BX1 is incident on the tomographic layer of interest LOI in the confronting manner) becomes the position 42p2. The state in which the X-ray generator 42 does not confront the tomographic layer of interest LOI (the state in which the irradiation axis of the X-ray beam BX1 is not incident on the tomographic layer of interest LOI in the confronting manner) becomes positions 42p0, 42p1, 42p3, 42p4. At this point, when the position 42p2 in the confronting state is compared to the positions 42p0, 42p1, 42p3 and 42p4 in the state, the position 42p2 in the confronting state is a position farther from the tomographic layer of interest LOI than the other positions. That is, the position 42p2 is set outside the normal imaging trajectory NT42 of the X-ray generator 42. The position 52p2 of the X-ray detector 52 in the confronting state is closer to the tomographic layer of interest LOI than the positions 52p0, 52p1, 52p3, 52p4 in the non-confronting state. The position 52p2 is set outside the normal imaging trajectory NT52 of the X-ray detector 52.

In the CT imaging, until the X-ray generator 42 reaches the position 42p2 of the confronting state after passing through the position 42p1 where the incident angle ANG1 becomes 45°, the X-ray generator 42 is gradually moved away from the tomographic layer of interest LOI, and the X-ray detector 52 is gradually caused to approach the tomographic layer of interest LOI. Until the X-ray generator 42 reaches the position 42p3 where the incident angle ANG1 becomes 135° from the position 42p2 of the confronting state, the X-ray generator 42 is gradually caused to approach the tomographic layer of interest LOI, and the line X-ray detector 52 is gradually moved away from the tomographic layer of interest LOI. That is, in the imaging trajectory PT42 of the X-ray generator 42, the position 42p1 to the position 42p3 are different from those of the normal imaging trajectory NT42, and other positions are matched. Similarly, in the imaging trajectory PT52 of the X-ray detector 52, the position 52p1 to the position 52p3 are different from those of the normal imaging trajectory NT52, and other positions are matched.

Figure 12:
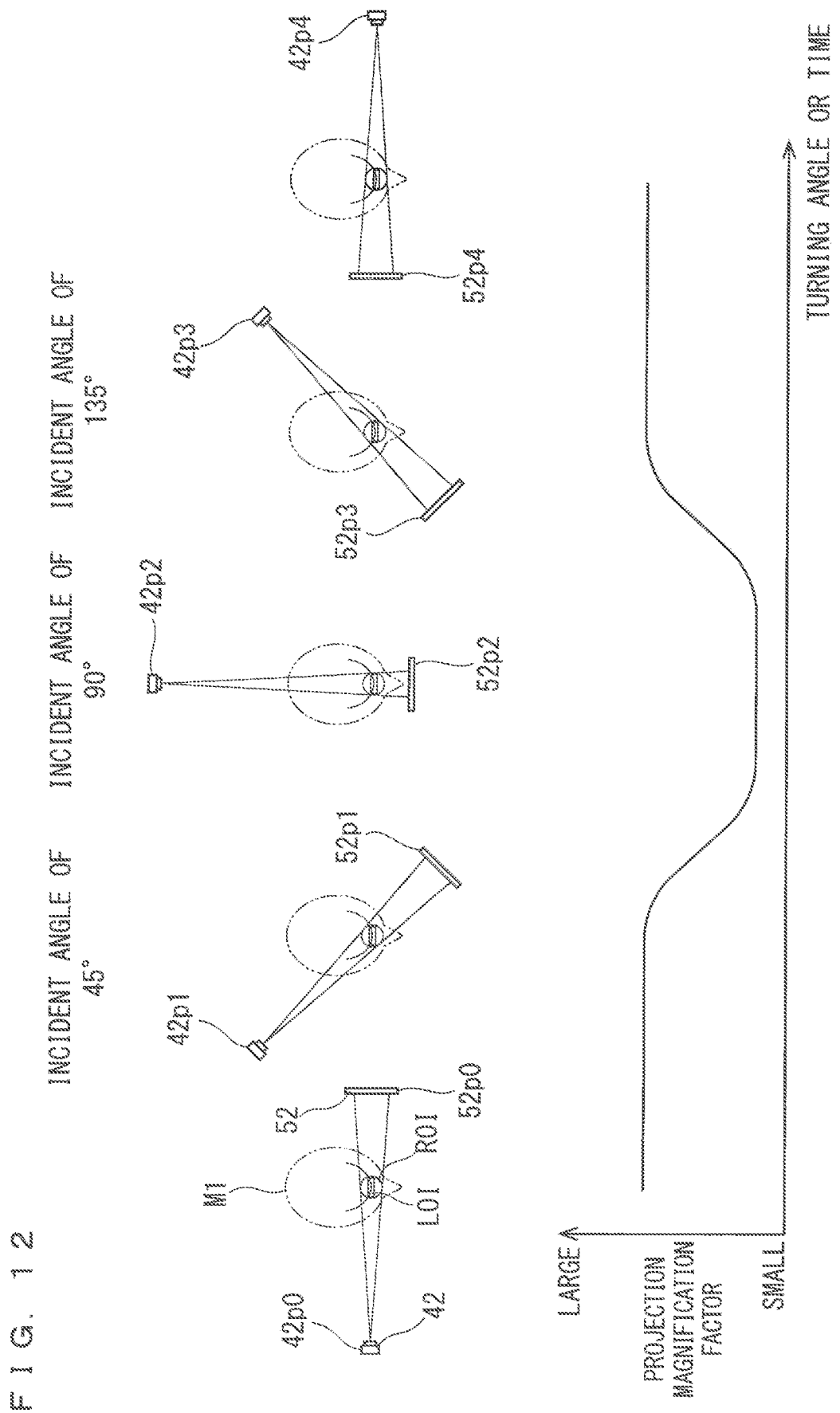
FIG. 12 is a view illustrating a fluctuation in a projection magnification factor according to turning angles of an X-ray generator 42 and an X-ray detector 52.

FIG. 12 is a view illustrating a fluctuation in the projection magnification factor according to the turning angles of the X-ray generator 42 and the X-ray detector 52. By setting the imaging trajectories PT42, PT52 as described above, as illustrated in FIG. 12, the projection magnification factor is kept constant until the incident angle ANG1 reaches 45°, and the projection magnification factor decreases gradually until the incident angle ANG1 becomes 90° after exceeding 45°. The projection magnification factor is minimized when the incident angle ANG1 is 90°. The projection magnification factor increases gradually until the incident angle ANG1 reaches 135° after the incident angle ANG1 exceeds 90°, and the projection magnification factor is kept constant after the incident angle ANG1 exceeds 135°. That is, the magnification factor decreased in the confronting state when the state in which the X-ray generator 42 confronts the tomographic layer of interest LOI (when the X-ray generator 42 is located at the position 42p2) and the state in which the X-ray generator 42 does not confront the tomographic layer of interest LOI (for example, when the X-ray generator 42 is located at the positions 42p0, 42p1, 42p3, 42p4) are compared to each other.

The magnification factor can be minimized only when the incident angle ANG1 is 90°. Alternatively, the minimized magnification factor can have a width. That is, the magnification factor can be maintained at the same minimum magnitude for a certain period from the timing at which the incident angle ANG1 is slightly less than 90°, through the timing at which the incident angle ANG1 is exactly 90°, and to the timing at which the incident angle ANG1 slightly exceeds 90°.

As described above, the imaging trajectory setting unit 306 sets the imaging trajectories PT42, PT52 of the X-ray generator 42 and the X-ray detector 52. The imaging controller 80 moves the X-ray generator 42 and the X-ray detector 52 along the imaging trajectories PT42, PT52 by controlling the operations of the turning drive unit 642 and the XY-direction movement drive unit 644. That is, the imaging controller 80 controls the XY-direction movement drive unit 644 according to the incident angle ANG1 while changing the incident angle ANG1 by controlling the operation of the turning drive unit 642. Consequently, the imaging controller 80 relatively decreases the projection magnification factor in the confronting state when the confronting state and the non-confronting state are compared to each other.

In the CT imaging, the turning is started from the position where the incident angle ANG1 becomes 0°. However, the turning is not necessarily started from the position where the incident angle ANG1 becomes 0°. For example, the turning of the X-ray generator 42 can be started from the position where the incident angle ANG1 becomes an angle larger than 0° or the position where the incident angle ANG1 becomes an angle smaller than 0° (the position where the center axis X-ray CBX1 is emitted on the opposite side to the confronting side with respect to the tomographic layer of interest LOI). Alternatively, the rotation of the X-ray generator 42 can be started from the near side in the rotational direction with respect to the position 42p0, and the emission of the X-ray beam BX1 can be started after the X-ray generator 42 reaches the position 42p0.

At this point, attention is paid to the turning center axis RA1 that is the turning center of the X-ray generator 42 and the X-ray detector 52. While the X-ray generator 42 moves from the position 42p0 to the position 42p1, and while the X-ray generator 42 moves from the position 42p3 to the position 42p4, the turning center axis RA1 is set to the center point CP1. On the other hand, while the X-ray generator 42 moves from the position 42p1 to the position 42p3, as indicated by an arrow D1 in FIG. 10, the turning center axis moves on a circular trajectory in which the X-ray generator 42 moves away from the center point CP1 and returns to the center point CP1.

When the shaft 66 that rotates the turning arm 62 is matched with the turning center axis RA1, the X-ray generator 42 and the X-ray detector 52 can be moved on the imaging trajectories PT42, PT52 by moving the shaft 66 on the trajectory of the turning center axis RA1 in FIG. 10. The shaft 66 is not necessarily matched with the turning center axis RA1. For example, the technique described in Japanese Patent Application Laid-Open No. 2007-29168 can also be applied to the present application. That is, while the shaft 66 is rotated, the shaft 66 is moved along a circumference of a predetermined radius centered on the center point CP1 of the imaging region ROI in the XY-plane. Consequently, the X-ray generator 42 and the X-ray detector 52 can be turned around the turning center axis RA1 matched with the center point CP1. In this case, the turning center axis RA1 is set at a position different from the shaft 66 that is the mechanical turning axis.

In the embodiment, the rotational movement and the movement in the XY-plane of the X-ray generator 42 and the X-ray detector 52 are performed by the rotation about the Z-axis of the shaft 66 of the turning arm 62 and the movement in the XY-plane. Thus, the setting of the imaging trajectories PT42, PT52 of the X-ray generator 42 and the X-ray detector 52 is equivalent to the setting of the position in the XY-plane of the shaft 66 according to the rotation amount of the shaft 66.

The description of the movement of the turning center axis RA1 will be further supplemented. The movement turning center axis RA1 moves as the rotation center at any time while the X-ray generator 42 and the X-ray detector 52 move along the magnification factor adjustment imaging trajectories PT42, PT52. In the normal CT imaging, an incident angle at which the incident angle ANG1 is an intermediate angle between 45° and 90° is set to an incident angle ANG1a, and an incident angle at which the incident angle ANG1 is 90° is set to an incident angle ANG1b. The center axis X-ray CBX1 at the incident angle ANG1a is set to a center axis X-ray CBX1A (not illustrated), and the center axis X-ray CBX1 at the incident angle ANG1b is set to a center axis X-ray CBX1B (not illustrated).

In the magnification factor adjustment CT imaging, as described above, because the movement turning center axis RA1 moves as the rotation center at any time, the position of the turning center axis RA1 at the incident angle ANG1a takes the position of, for example, RA1a in FIG. 10, and the position of the turning center axis RA1 at the incident angle ANG1b takes the position of, for example, RA1b in FIG. 10.

The center axis X-ray CBX1 at the incident angle ANG1a is a center axis X-ray CBX1a matched with the center axis X-ray CBX1A in an incident angle manner, and the center axis X-ray CBX1 at the incident angle ANG1b is a center axis X-ray CBX1b matched with the center axis X-ray CBX1B in the incident angle manner.

As described above, the incident angle is caused to correspond to the incident angle in the normal CT imaging in which the turning center is fixed to one point, and the approach and the movement away of the X-ray generator 42 and the X-ray detector 52 are changed with respect to the imaging region during the imaging, which allows the magnification factor adjustment CT imaging to be performed.

In the illustrated example, the position RA1b of the turning center axis RA1 at the incident angle of 90° is located at a peak separated from the center point CP1. Assuming that the position of the turning center axis RA1 when located on the center point CP1 is a position RA10, the degree of separation of the position RA1a from the center point CP1 is equal to the degree between the position RA10 and the position RA1b. That is, although the position RA1a is separated farther from the center point CP1 than the position RA10, the degree of the position RA1a is not as large as that of the position RA1b.

In the illustrated magnification factor adjustment CT imaging, it can be seen that the position of the turning center axis RA1 moves on the axial line of the center axis X-ray CBX1 at each timing at which the incident angle changes. At this point, the position of the turning center axis RA1 gradually changes such that a degree of separation of the turning center axis RA1 from the center point CP1 peaks while the center axis X-ray CBX1 is incident on the tomographic layer of interest LOI in the confronting manner.

The degree of separation is maintained so as to be maximized not only in the state in which the center axis X-ray CBX1 is incident on the tomographic layer of interest LOI in the confronting manner, but also in the period of good incident angles close to the confronting state.

As described above, in the imaging unit 20 of the embodiment, the projection magnification factor is decreased when the X-ray generator 42 confronts the tomographic layer of interest LOI, so that the blurring caused by the size of the focal plane 420 can be reduced on the X-ray projection image when the tomographic layer of interest LOI is projected from the front surface. That is, the X-ray projection image can be acquired with high resolution when the tomographic layer of interest LOI is projected from the front surface. Thus, the image quality of the tomographic image obtained when the image processor 308 reconstructs the tomographic layer of interest LOI can be improved.

In the X-ray imaging, the X-ray detector 52 is caused to approach the tomographic layer of interest LOI by limiting to a part of the entire turning range in which the X-ray generator 42 and the X-ray detector 52 are turned, which prevents the X-ray detector 52 from contacting with the subject M1. The X-ray generator 42 is moved away from the tomographic layer of interest LOI by limiting to a part of the entire turning range, so that the X-ray generator 42 or the X-ray generation unit 40 accommodating the X-ray generator 42 and one end of the turning arm 62 supporting the X-ray generation unit 40 can be prevented from colliding with another member (such as the post 70).

The X-ray generation controller 810 controls the operation of the X-ray regulating unit 44 according to the movement of the X-ray generator 42 away from the tomographic layer of interest LOI during the turning, so that the emission range of the X-ray beam BX1 (a spread angle (fan angle) about the Z-axis of the X-ray beam BX1) can be decreased. Consequently, the range wider than the imaging region ROI can be prevented from being irradiated with the X-ray beam BX1, so that an X-ray exposure dose of the subject M1 can be reduced.

In the CT imaging of FIG. 10, as described above with reference to FIG. 7, the setting of the imaging region ROI is received such that the imaging region ROI includes at least a part of the dental arch DA1, and the tomographic layer of interest LOI can be set along a part of the dental arch DA1 set in the imaging region ROI. Consequently, because the tomographic image along the dental arch DA1 can be acquired, the tomographic image suitable for a dental diagnosis can be acquired. The dental arch DA1 is unevenly distributed in front of the head of the subject M1, and extends along a front edge of the head. For this reason, the setting of the tomographic layer of interest LOI along the dental arch can cause the X-ray detector 52 to approach the head when the X-ray generator confronts the tomographic layer of interest LOI. Thus, the high-resolution X-ray tomographic image can easily be acquired.

FIG. 13 is a view illustrating an example of the X-ray imaging. The X-ray imaging in FIG. 13 is CT imaging in which the vicinity of a right molar in the jaw of the subject M1 is set to the imaging region ROI. In the CT imaging, the X-ray generator 42 is turned by 180° from the position 42p0 on the right rear side of the head of the subject M1 to the position 42p4 on the left front side of the head, and the X-ray detector 52 is turned by 180° from the position 52p0 on the left front side of the head of the subject M1 to the position 52p4 on the right rear side of the head.

In the CT imaging, when the X-ray generator 42 confronts the tomographic layer of interest LOI, namely, when the center axis X-ray CBX1 emitted from the X-ray generator 42 is incident on the tomographic layer of interest LOI at right angles, the X-ray generator 42 passes through the position 42p2 where the X-ray generator 42 is moved away from the tomographic layer of interest LOI, and the X-ray detector 52 passes through the position 52p2 where the X-ray detector 52 approaches the tomographic layer of interest LOI. Consequently, the projection magnification factor can be decreased in the confronting state.

In the CT imaging of FIG. 10, the tomographic layer of interest LOI is set along the front teeth of the jaw. A convex nose is located on one side in the normal direction of the tomographic layer of interest LOI. For this reason, it is necessary that the imaging trajectory setting unit 306 set the imaging trajectory PT52 such that the X-ray detector 52 does not contact with the nose. On the other hand, in the CT imaging of FIG. 13, the tomographic layer of interest LOI is set along the right molar in the jaw of the subject M1. On one side in the normal direction of the tomographic layer of interest LOI, a concave portion such as the nose does not exist, but only a cheek exists. Thus, the imaging trajectory setting unit 306 can set the imaging trajectory PT52 such that the X-ray detector 52 is closer to the tomographic layer of interest LOI as compared to the case of the CT imaging in FIG. 10.

The CT imaging in FIGS. 10 and 13 is the CT imaging in which the X-ray generator 42 and the X-ray detector 52 are turned by 180°. However, the turning angles of the X-ray generator 42 and the X-ray detector 52 are not limited to 180°.

Figure 14:
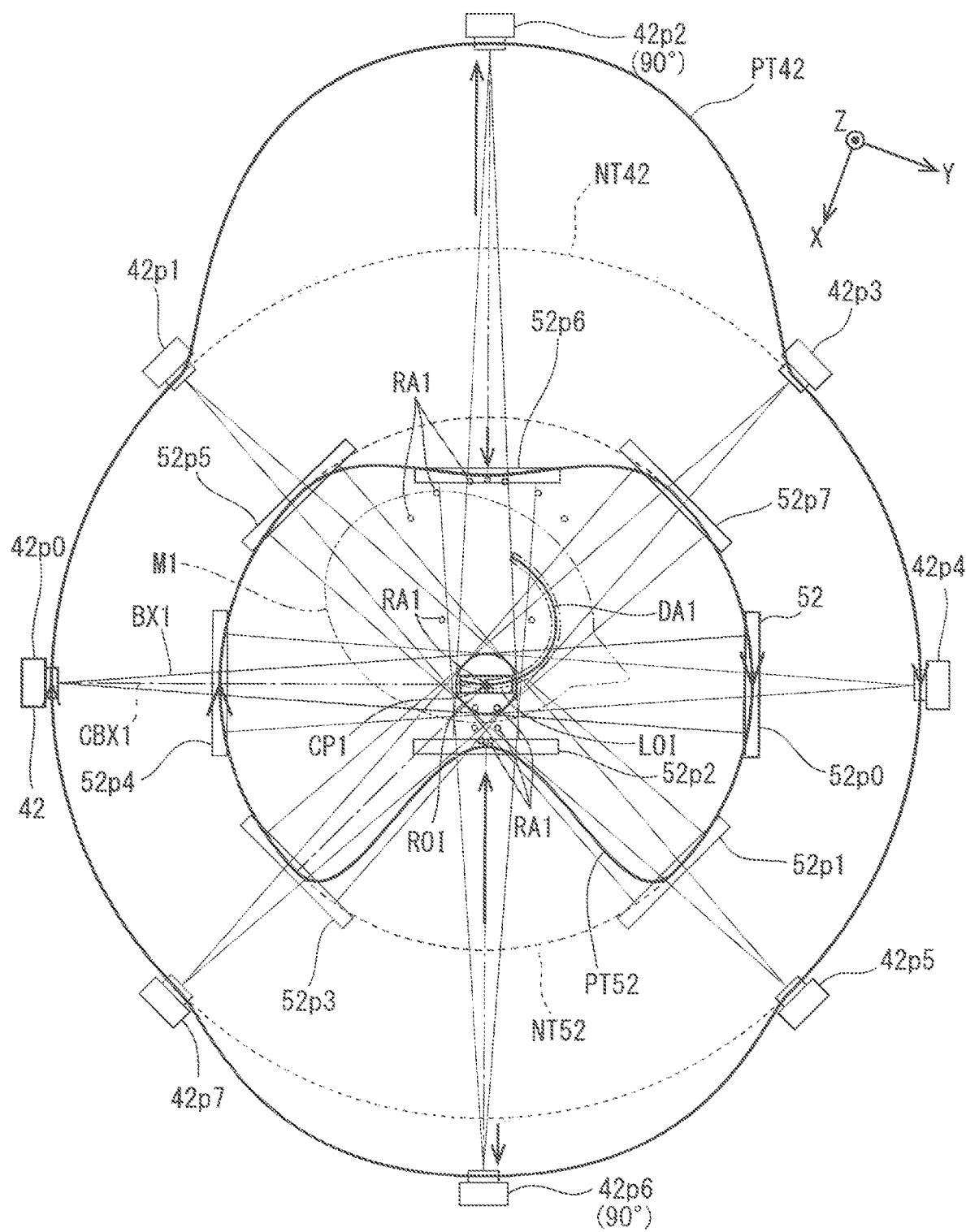
FIG. 14 is a view illustrating an example of the X-ray imaging.

FIG. 14 is a view illustrating an example of the X-ray imaging. The X-ray imaging in FIG. 14 is the CT imaging, in which the vicinity of the right molar in the jaw is set to the imaging region ROI and a part of the dental arch DA1 is included in the imaging region ROI. The tomographic layer of interest LOI is the region extending linearly along the tangential line of a part of the dental arch DA1 included in the imaging region ROI.

In the CT imaging, the X-ray generator 42 is turned by 360° from the position 42$p$0 at the right rear side of the head of the subject M1 to the position 42$p$0 after passing through each of the positions 42$p$1 to 42$p'$7. The X-ray detector 52 is turned by 360° from the position 52$p$0 on the left front side of the head of the subject M1 to the position 52$p$0 after passing through each of the positions 52$p$1 to 52$p$7.

Assuming that the direction from the center of the head is an hour hand of a clock, the nose of the head is expressed as 12 o'clock, the back of the head is expressed as 6 o'clock, a right ear is expressed as 3 o'clock, and a left ear is expressed as 9 o'clock. During the CT imaging, the center axis X-ray CBX1 confronts the tomographic layer of interest LOI while being orthogonal to the tomographic layer of interest LOI when the subject M1 is irradiated with the X-ray beam BX1 from the right side of the subject M1 (specifically, between 12 o'clock and 3 o'clock, and the right side when the entire head is roughly divided into the left and the right) (when the X-ray generator 42 passes through the position 42$p$2 and the X-ray detector 52 passes through the position 52$p$2), and when the subject M1 is irradiated with the X-ray beam BX1 from the left side of the subject M1 (specifically, between 6 o'clock and 9 o'clock, and the left side when the entire head is roughly divided into the left and the right) (when the X-ray generator 42 passes through the position 42$p$6 and the X-ray detector 52 passes through the position 52$p$6).

In the CT imaging, when the X-ray generator 42 confronts the tomographic layer of interest LOI, the X-ray generator 42 passes through the positions 42$p$2, 42$p$6. The positions 42$p$2, 42$p$6 are positions moved farther away from the tomographic layer of interest LOI than the position (for example, the positions 42$p$0, 42$p$1, 42$p$3 to 42$p$5, 42$p'$7) of the X-ray generator 42 when the X-ray generator 42 does not confront the tomographic layer of interest LOI. In the CT imaging, when the X-ray generator 42 confronts the tomographic layer of interest LOI, the X-ray detector 52 passes through the positions 52$p$2, 52$p$6. The positions 52$p$2, 52$p$6 are positions moved farther away from the tomographic layer of interest LOI than the position (for example, the positions 52$p$0, 52$p$1, 52$p$3 to 52$p$5, 52$p$7) of the X-ray detector 52 when the X-ray generator 42 does not confront the tomographic layer of interest LOI. Consequently, when the X-ray generator 42 confronts the tomographic layer of interest LOI, the projection magnification factor is decreased as compared with the case where the X-ray generator 42 does not confront the tomographic layer of interest LOI.

The confronting state when the X-ray generator 42 passes through the position 42$p$2 is set to a first confronting state, and the confronting state when the X-ray generator 42 passes through the position 42$p$6 is set to a second confronting state. The position 52$p$2 of the X-ray detector 52 in the first confronting state is closer to the tomographic layer of interest LOI than the position 52$p$6 of the X-ray detector 52 in the second confronting state. Because the target imaging region ROI is unevenly distributed on the right side (between 12 o'clock and 3 o'clock) of the head of the subject M1, the X-ray detector 52 can be caused to approach the imaging region ROI as compared to the case of the irradiation from the right side (between 12 o'clock and 3 o'clock) when the subject M1 is irradiated with the X-ray beam BX1 from the left side (between 6 o'clock and 9 o'clock) of the subject M1.

The trajectories PT42, PT52 can be corrected when another mechanical element interferes with the turning of the X-ray generator 42 and the X-ray detector 52. For example, when the post 70 exists between the positions 42$p$5 to 42$p'$7 of the trajectory of the X-ray generator 42 (the trajectory of the X-ray detectors 52 ranges from the position 52$p$5 to the position 52$p$7), the trajectories PT42, PT52 can appropriately be corrected so as to avoid the post 70.

In the X-ray imaging of FIGS. 10 to 14, only one tomographic layer of interest LOI is set in the imaging region ROI. However, the tomographic layer of interest LOI set in the imaging region ROI is not limited to one.

Figure 15:
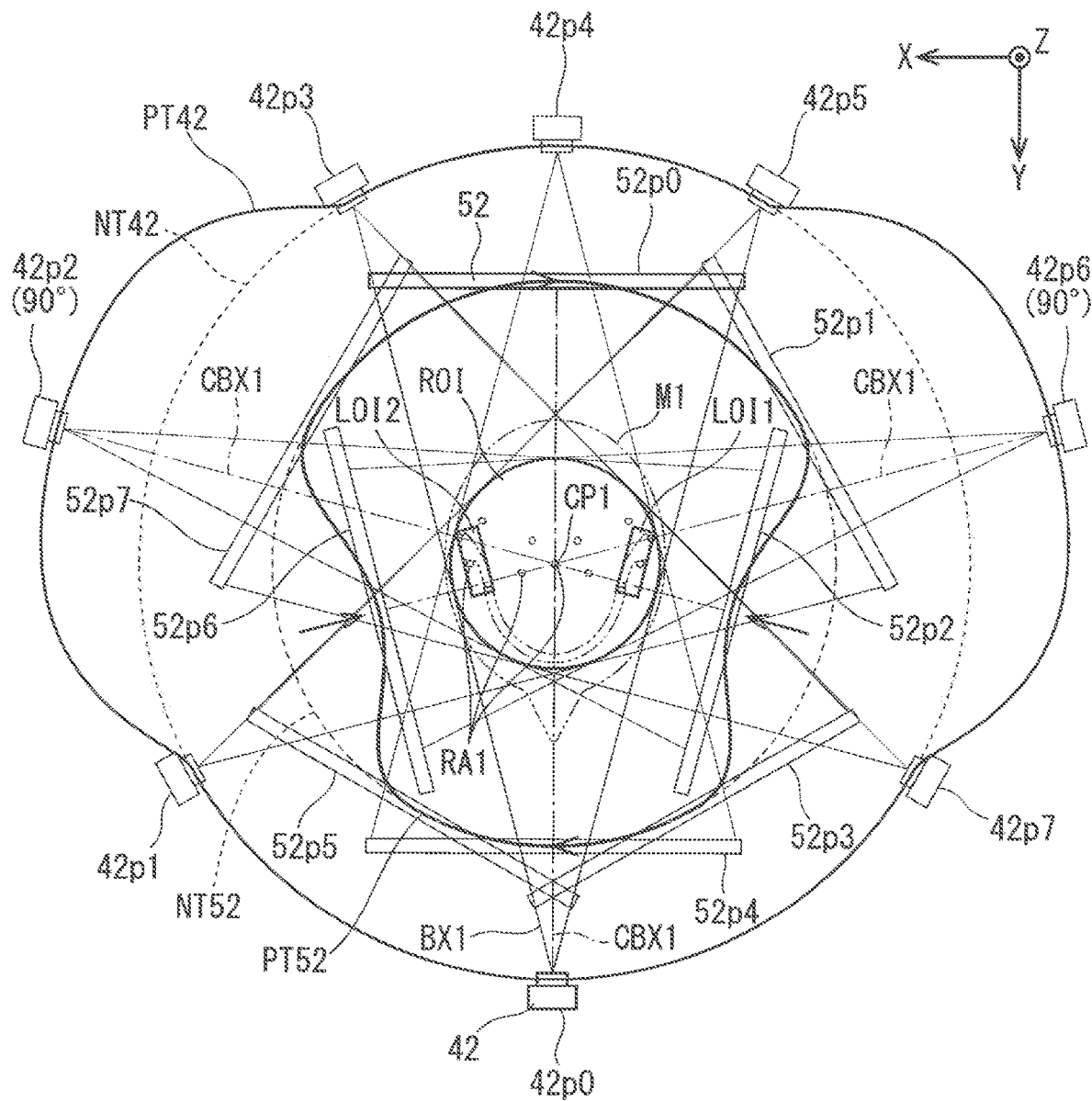
FIG. 15 is a view illustrating an example of the X-ray imaging.

FIG. 15 is a view illustrating an example of the X-ray imaging. The X-ray imaging in FIG. 15 is the CT imaging, in which the entire jaw of the subject M1 is set to the imaging region ROI and two tomographic layers of interest LOI1, LOI2 are set inside the imaging region ROI. At this point, the tomographic layers of interest LOI1, LOI2 are set to the left temporomandibular joint and the right temporomandibular joint, respectively.

In the CT imaging, the X-ray generator 42 is turned by 360° from the position 42$p$0 in front of the head of the subject M1 to the position 42$p$0 after passing through the positions 42$p$1 to 42$p'$7. The X-ray detector 52 is turned by 360° from the position 52$p$0 on the rear side of the head of the subject M1 to the position 52$p$0 after passing through the positions 52$p$1 to 52$p'$7.

In the CT imaging, when the X-ray generator 42 confronts a tomographic layer of interest LOI1, the position 42$p$2 through which the X-ray generator 42 passes is farther from the tomographic layer of interest LOI1 as compared with the position (for example, positions 42$p$0, 42$p$1, 42$p$3 to 42$p$5, 42$p'$7) in the non-confronting state. When the X-ray generator 42 confronts the tomographic layer of interest LOI1, the position 52$p$2 through which the X-ray detector 52 passes is closer to the tomographic layer of interest LOI than the position (for example, positions 52$p$0, 52$p$1, 52$p$3 to 52$p$5, 52$p$7) in the non-confronting state. For this reason, when the X-ray generator 42 confronts the tomographic layer of interest LOI1, the projection magnification factor can relatively decreased smaller than the non-confronting state.

The position 42$p$6 through which the X-ray generator 42 passes when the X-ray generator 42 confronts a tomographic layer of interest LOI2 is farther from the tomographic layer of interest LOI2 than the positions (for example, the positions 42$p$0, 42$p$1, 42$p$3 to 42$p$5, 42$p'$7) in the non-confronting state. When the X-ray generator 42 confronts the tomographic layer of interest LOI2, the position 55p6 through which the X-ray detector 52 passes is closer to the tomographic layer of interest LOI2 than the position (for example, positions 52p0, 52p1, 52p3 to 52p5, 52p7) in the non-confronting state. Consequently, the projection magnification factor can be decreased when the X-ray generator 42 confronts the tomographic layer of interest LOI2.

The position 42p6 is the position when the X-ray generator 42 does not confront the tomographic layer of interest LOI1. It is also assumed that the position 42p2 is closer to the tomographic layer of interest LOI1 than the position 42p6. That is, the position 42p2 through which the X-ray generator 42 passes when confronting the tomographic layer of interest LOI1 is not necessarily farther from the tomographic layer of interest LOI1 than all the positions through which the X-ray generator 42 passes when the X-ray generator 42 does not confront the tomographic layer of interest LOI1. That is, the position 42p2 can be farther from the tomographic layer of interest LOI1 than at least a part of all the positions through which the X-ray generator 42 passes when the X-ray generator 42 does not confront the tomographic layer of interest LOI1.

Similarly, the position 52p6 is the position of the X-ray detector 52 when the X-ray generator 42 does not confront the tomographic layer of interest LOI, but it is assumed that the position 52p6 is located closer to the tomographic layer of interest LOI than the position 52p2. That is, the position 52p2 can be closer to the tomographic layer of interest LOI1 than at least a part of all the positions through which the X-ray detector 52 passes when the X-ray generator 42 does not confront the tomographic layer of interest LOI1.

In the CT imaging of FIG. 15, the projection magnification factor is decreased when the X-ray generator 42 confronts the tomographic layer of interest LOI1 while turning on the right side of the subject M1. However, the projection magnification factor can be decreased when the X-ray generator 42 confronts the tomographic layer of interest LOI1 while turning on the left side of the subject M1 (when the X-ray generator 42 passes through the side opposite to the position 42p2). Similarly, in the CT imaging of FIG. 15, the projection magnification factor is decreased when the X-ray generator 42 confronts the tomographic layer of interest LOI2 while turning on the left side of the subject M1. However, the projection magnification factor can be decreased when the X-ray generator 42 confronts the tomographic layer of interest LOI2 while turning on the left side of the subject M1 (that is, when the X-ray generator 42 passes through the side opposite to the position 42p6).

As described above, while the height of the head MEI is kept constant by the Z-direction drive unit 646 and the elevation drive unit 728, the support 60 is elevated or lowered with respect to the head MH by the relative movement, which allows the X-ray irradiation location to be changed in the Z-axis direction. For this reason, for example, the plurality of imaging regions located at different height positions can continuously be imaged such that one of the tooth rows of the upper jaw and the lower jaw is continuously imaged after the other is imaged. In this case, different regions of the dental arch can be set to the imaging target in each height position such that a front-tooth region is set in the upper jaw and a molar region is set in the lower jaw.

Figure 16:
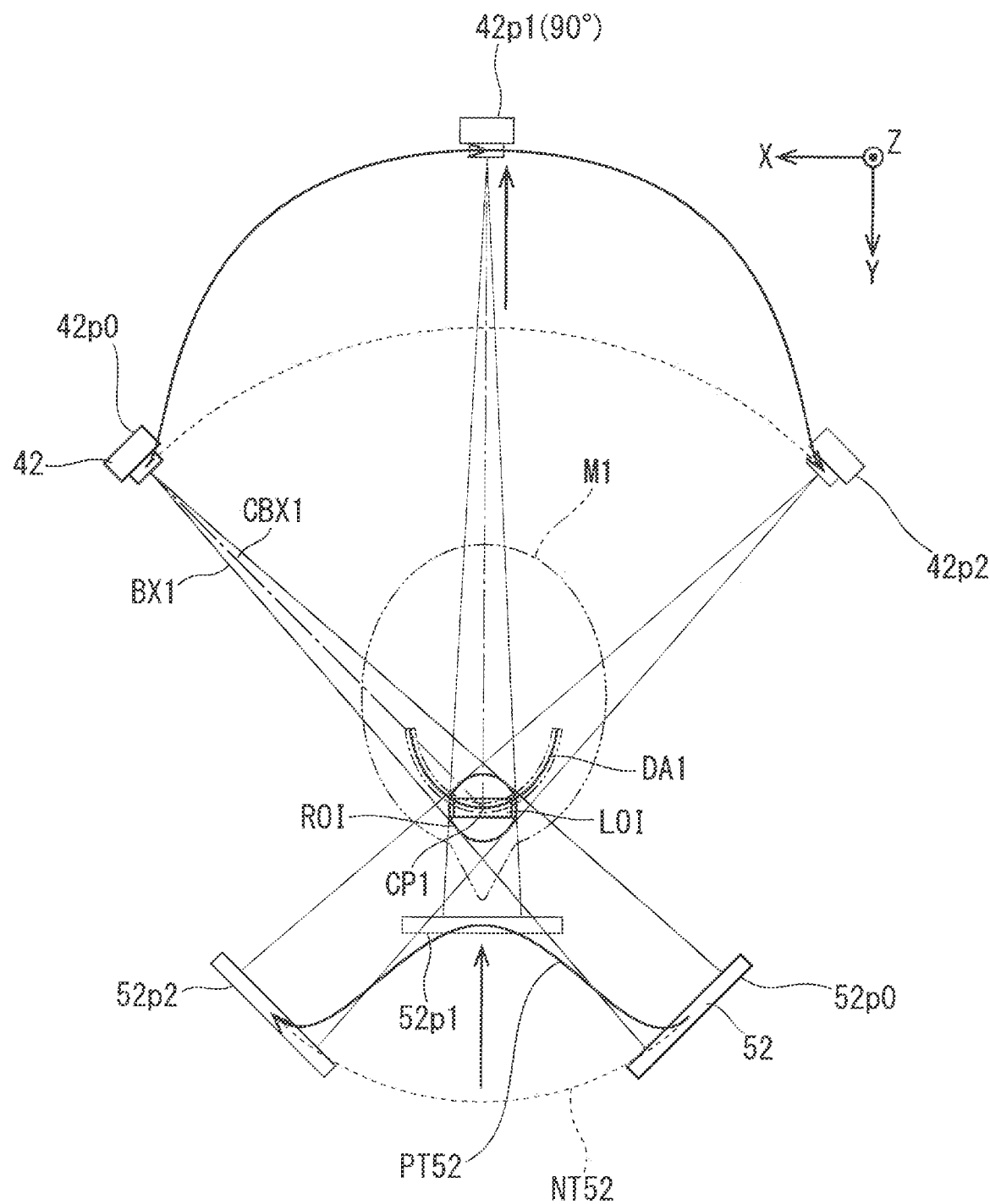
FIG. 16 is a view illustrating an example of the X-ray imaging.

FIG. 16 is a view illustrating an example of the X-ray imaging. The X-ray imaging in FIG. 16 is tomosynthesis imaging in which the X-ray generator 42 and the X-ray detector 52 are turned by an angle less than 180° around the head of the subject M1. For example, the turning angle can be set to 90° or 60°. Any angle less than 180° can be set by the operation, and any angle between 90° and 60° can be set by the operation. In the tomosynthesis imaging, as illustrated in FIG. 16, the X-ray projection image is acquired by rotating the X-ray generator 42 and the X-ray detector 52 to the left and right by a required angle around the incident angle ANG1 at which the X-ray generator 42 confronts the tomographic layer of interest LOI to be observed by an observer. In the tomosynthesis imaging, an X-ray tomographic images having relatively high quality can be acquired by reconstruction with respect to the tomographic layer of interest LOI. Since the X-ray irradiation less than only 180° is performed, the tomosynthesis imaging has an advantage that an imaging time can be shortened while the X-ray exposure dose of the subject M1 is reduced as compared with the CT imaging.

In the tomosynthesis imaging of FIG. 16, the imaging region ROI is set in the vicinity of the front teeth of the jaw of the subject M1, and the tomographic layer of interest LOI is set along the portion of the dental arch DA1 included in the imaging region ROI. The X-ray generator 42 is turned from the position 42p0 on the right rear side of the subject M1 to the position 42p2 on the left rear side, and the X-ray detector 52 is turned from the position 52p0 on the right front side of the subject M1 to the position 52p2 on the left front side. When the X-ray generator 42 confronts the tomographic layer of interest LOI, the imaging trajectories of the X-ray generator 42 and the X-ray detector 52 are set such that the X-ray generator 42 passes through the position 42p1 and the X-ray detector 52 passes through the position 52p1. The position 42p1 of the X-ray generator 42 is farther from the tomographic layer of interest LOI than the position (for example, the positions 42p0, 42p2) of the X-ray generator 42 when the X-ray generator 42 does not confront the tomographic layer of interest LOI. The position 52p1 is closer to the tomographic layer of interest LOI than the position (for example, the positions 52p0, 52p2) of the X-ray detector 52 when the X-ray generator 42 does not confront the tomographic layer of interest LOI. The setting of the imaging trajectory in this manner decreases the projection magnification factor during the confrontation, so that the high-quality X-ray tomographic image can be generated with respect to the tomographic layer of interest LOI.

<Flowchart of X-Ray Imaging>

Figure 17:
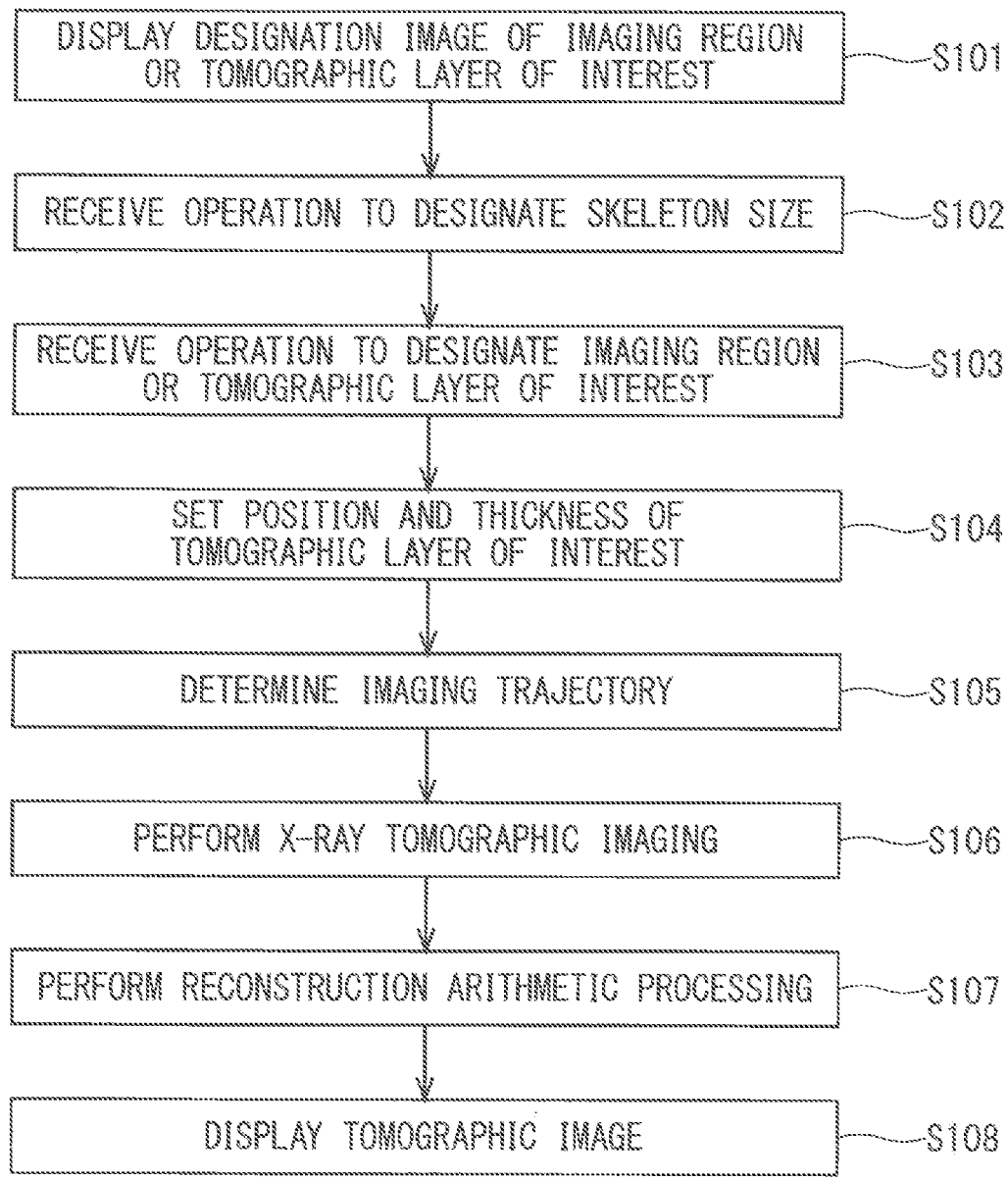
FIG. 17 is a flowchart illustrating operation of the X-ray tomography apparatus 10.

FIG. 17 is a flowchart illustrating the operation of the X-ray tomography apparatus 10. In the following description, it is assumed that positioning of the subject M1 in the imaging unit 20 is already completed.

The information processor 30 causes the display 32 to display the designation image for designating the tomographic layer of interest LOI or the imaging region ROI (step S101). For example, as illustrated in FIGS. 4 to 8, the designation image is a schematic diagram IL1 in which the site of interest is drawn, or a transmission image (such as a panoramic X-ray image IL2) obtained by the X-ray imaging of the subject M1.

Subsequently, the information processor 30 receives an operation to designate a skeleton size (step S102). For example, when the operator inputs the physical characteristics (such as the gender, the age, the height, and the weight) of the subject M1, the information processor 30 acquires the skeleton size corresponding to the input physical characteristics from a predetermined database. In each size, a standard size can be set from statistical data. The acquired skeleton size is used to approximately match the position of the imaging target site of the subject M1 disposed in the imaging unit 20 with the position of the imaging target site in the designation image.

When the transmission image (such as a panoramic X-ray image IL2) obtained by the X-ray imaging of the subject M1 is used as the designation image, step S102 can be skipped. When the skeleton size is designated in step S102, the information processor 30 can re-display the designation image matched with the designated skeleton size on the display 32. For example, the schematic diagram IL1 for each physical characteristic is previously prepared, and the schematic diagram IL1 corresponding to the specified physical characteristic can be displayed.

Subsequently, the information processor 30 receives an operation to designate the tomographic layer of interest LOI or the imaging region ROI (step S103). For example, the operation to designate the tomographic layer of interest LOI or the imaging region ROI is described with reference to FIGS. 4 to 8. In step S103, each of the tomographic layer of interest LOI and the imaging region ROI can individually be designated. As described above with reference to FIG. 7, the tomographic layer of interest LOI can automatically be set according to the designation of the imaging region ROI. The imaging region ROI can automatically be set according to the designation of the tomographic layer of interest LOI.

Subsequently, the tomographic layer-of-interest setting unit 304 sets the position and the thickness of the tomographic layer of interest LOI based on the designation operation received in step S103.

Subsequently, the imaging trajectory setting unit 306 determines the imaging trajectories PT42, PT52 of the X-ray generator 42 and the X-ray detector 52 based on the position and the thickness of the tomographic layer of interest set in step S104 (step S105). Specifically, as described above with reference to FIGS. 10 to 16, the imaging trajectory setting unit 306 determines the imaging trajectories PT42, PT52 such that the projection magnification factor when the X-ray generator 42 confronts the tomographic layer of interest LOI is smaller than the projection magnification factor when the X-ray generator 42 does not confront the tomographic layer of interest LOI.

In order to prevent the X-ray detector 52 from contacting with the subject M1, for example, a prohibited space in which the entry of the X-ray detector 52 is prohibited can previously be defined in the real space where the subject M1 is disposed. In this case, the imaging trajectory setting unit 306 can set the imaging trajectory PT52 such that the X-ray detector 52 does not enter the prohibited space. The prohibited space can be expanded or reduced as appropriate based on the physical characteristics of the subject M1, such as the skeletal data set in step S102.

Similarly, in order to prevent the X-ray generation unit 40 accommodating the X-ray generator 42 and the like from contacting with another member, a movable space through which the X-ray generator 42 can pass can previously be defined in the imaging unit 20. In this case, the imaging trajectory setting unit 306 can set the imaging trajectory PT42 such that the X-ray generator 42 moves in the movable space.

The imaging trajectories PT42, PT52 set previously in each of the different imaging regions ROI or tomographic layers of interest LOI can be stored in the storage 31. In this case, the imaging trajectory setting unit 306 can read the imaging trajectories PT42, PT52 matched with the set imaging region ROI or tomographic layer of interest LOI from the storage 31.

In step S105, when the imaging trajectories PT42, PT52 are determined, the imaging unit 20 performs the X-ray imaging (step S106). Specifically, data of the imaging trajectories PT42, PT52 are sent to the imaging controller 80. Based on the data, the turning controller 802 controls the operation of the turning drive unit 642, and the XY-direction movement controller 804 controls the operation of the XY-direction movement drive unit 644. The imaging unit 20 captures the X-ray projection image of the imaging region ROI projected on the detection surface of the X-ray detector 52 at a predetermined frame rate. The captured X-ray projection image is appropriately stored in the storage 31 or the like of the information processor 30.

Subsequently, the image processor 308 performs reconstruction arithmetic processing on the plurality of X-ray projection images acquired in step S106 (step S107). Specifically, the image processor 308 generates three-dimensional volume data of the imaging region ROI by a filter correction back projection method (FBP method), a superposition integration method, or the like. The image processor 308 generates the X-ray tomographic image representing the tomographic layer of interest LOI based on the three-dimensional volume data. Although being concentrated on and around the tomographic layer of interest LOI, three-dimensional image data having a certain thickness can also be generated in the tomosynthesis imaging, and the X-ray tomographic image representing the tomographic layer of interest LOI can be generated.

At this point, the projection magnification factor varies among the plurality of X-ray projection images. In performing the reconstruction arithmetic processing, the image size can be converted such that the projection magnification factors are matched with each other between the X-ray projection images. Consequently, parallelization of arithmetic processing is promoted, so that the time necessary for the arithmetic processing can be shortened when an arithmetic processing apparatus (such as a GPU) excellent in parallel processing is used.

When the X-ray tomographic image is generated for the tomographic layer of interest LOI, the X-ray tomographic image is displayed on the display 32 (step S108).

<Determination of Incident Angle ANG1 at Beginning of Approach of X-Ray Generator 42 Based on Tomographic Thickness>

The incident angle ANG1 when the X-ray generator 42 starts the approach to the tomographic layer of interest LOI can be an established one, or can be appropriately set according to the tomographic thickness TN1 of the tomographic layer of interest LOI. In the latter case, for example, the operation unit 34 or the operation panel 84 can receive the input of the tomographic thickness TN1 from the operator. The imaging trajectory setting unit 306 can set the imaging trajectories PT42, PT52 according to the tomographic thickness TN1 while the tomographic layer-of-interest setting unit 304 of the information processor 30 sets the tomographic layer of interest LOI having the input tomographic thickness TN1. In this case, the tomographic layer-of-interest setting unit 304 and the operation unit 34 or the operation panel 84 are an example of the configuration of the tomographic thickness designation receiving unit.

The relationship between the tomographic thickness TN1 and the incident angle ANG1 when the X-ray generator 42 is moved away from the tomographic layer of interest LOI (when the X-ray detector 52 approaches the tomographic layer of interest LOI) will be described below. FIG. 23 is a view illustrating the fluctuation in the projection magnification factor according to the incident angle ANG1. In this example, the projection magnification factor is decreased to P when the X-ray generator 42 confronts (looks straight at) the tomographic layer of interest LOI (when the incident angle ANG1 is) 90°. Moreover, in this example, the X-ray detector 52 is caused to approach the tomographic layer of interest LOI such that the incident angle AGN1 has the substantially constant low projection magnification factor P between 90°−Θ and 90°+Θ. An incident angle θs when the X-ray detector 52 starts to approach the tomographic layer of interest LOI and an incident angle θx when the approach is completed are smaller than 90°−Θ. An incident angle θe when the X-ray detector 52 starts to move away from the tomographic layer of interest LOI and an incident angle θz when the movement away is completed are larger than 90°+Θ.

When the imaging as described above is performed, the following equation (1) holds between the angle Θ that decreases the projection magnification factor and a tomographic thickness σ (mm) obtained with projection data of the low projection magnification factor.

$$1/\sigma = \zeta \sin \Theta \qquad \text{equation (1)}$$

Where "ζ" is resolution (LP/mm) when the projection magnification factor is decreased.

According to the equation (1), when the angle Θ is brought close to 0, namely, when the range where the projection magnification factor is decreased is narrowed, the tomographic thickness σ increases relatively. When the angle Θ is set to 0°, σ becomes infinite (that is, equivalent to a simple projection image). That is, projection data having the low projection magnification factor can be obtained only when the X-ray generator 42 confronts the tomographic layer of interest LOI. On the other hand, when the angle Θ is brought close to 90°, the tomographic thickness σ decreases relatively. For example, when the angle Θ is set to 90°, the projection data for 180° is obtained at the low projection magnification factor, and the tomographic thickness σ is 1/ζ of the limit.

As described above, Θ is determined based on the equation (1) when the operator designates the tomographic thickness TN1(σ) of the tomographic layer of interest LOI, so that the incident angle range 90°−Θ to 90°+Θ decreasing the projection magnification factor can be determined. Based on the range of the incident angle, the imaging trajectory setting unit 306 can determine the incident angle θs when the X-ray detector 52 starts to approach the tomographic layer of interest LOI, the incident angle θx (smaller than 90°−Θ) when the approach is completed, the incident angle θe at which the X-ray detector 52 starts to move away from the tomographic layer of interest LOI, and the incident angle θz (larger than 90°+Θ) at which the movement away is completed, and set the imaging trajectories PT42, PT52. In this case, the imaging trajectory setting unit 306 functions as a controller that determines the incident angle when the X-ray detector 52 is caused to approach the tomographic layer of interest LOI according to the designated tomographic thickness. The X-ray tomographic image illustrating the tomographic layer of interest LOI of the designated tomographic thickness can suitably be acquired by determining the suitable incident angle when the magnification factor is changed according to the designated tomographic thickness.

2. MODIFICATIONS

Although the embodiment is described above, the present invention is not limited to the above embodiment, and various modifications can be made. Modification of the above embodiment will be described below. In the following description, the element having the function similar to that of the already described element is denoted by the identical reference numeral or the reference numeral to which an alphabetical letter is added, and sometimes the detailed description will be omitted.

First Modification

Figure 18:
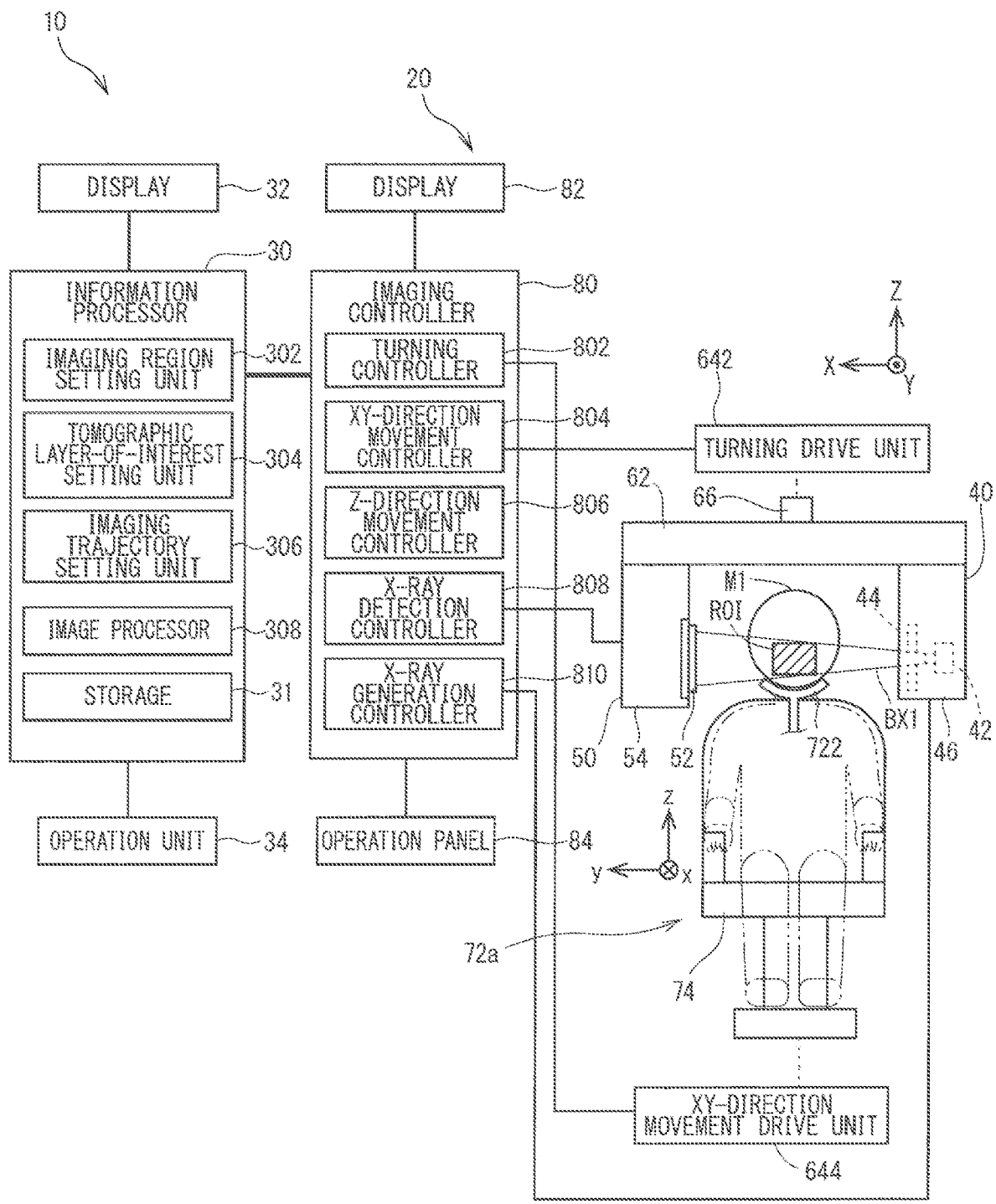
FIG. 18 is a view illustrating a configuration of an X-ray tomography apparatus 10 according to a modification.

FIG. 18 is a view illustrating a configuration of an X-ray tomography apparatus 10 according to a modification. The subject holder 72 of this modification includes a subject chair 74 on which the subject M1 is seated. In the above embodiment, the XY-direction movement drive unit 644 translates the turning arm 62 in the XY-plane by moving the shaft 66 in the X-axis direction and the Y-axis direction. As a result, the X-ray generator 42 and the X-ray detector 52 move relative to the subject M1 in the X-axis direction and the Y-axis direction. On the other hand, in this modification, the XY-direction movement drive unit 644 is connected to the subject chair 74, and moves the subject chair 74 in the X-axis direction and the Y-axis direction. Consequently, the subject M1 moves relative to the X-ray generator 42 and the X-ray detector 52 of the turning arm 62 in the X-axis direction and the Y-axis direction.

For the X-ray tomography apparatus 10 of this modification, when the projection magnification factor is decreased during the X-ray imaging, the subject chair 74 is moved to move the subject M1 to an appropriate position during the X-ray imaging. That is, when the X-ray generator 42 confronts the tomographic layer of interest LOI, the portion corresponding to the tomographic layer of interest LOI is moved away from the X-ray generator 42, and caused to approach the X-ray detector 52. Consequently, the projection magnification factor can be decreased in the confronting state.

In the imaging unit 20 of the embodiment, the turning drive unit 642 rotates the turning arm 62 to turn the X-ray generator 42 and the X-ray detector 52 around the subject M1. However, the turning drive unit 642 can rotate the subject holder to rotate the subject.

The imaging unit 20 of the embodiment does not necessarily include the turning arm 62. For example, while the X-ray generation unit 40 and the X-ray detection unit 50 are attached to a ring-shaped annular member, the X-ray generation unit 40 and the X-ray detection unit 50 can move along the circumferential direction of the annular member. In this case, a virtual axis passing through the center of the annular member is the turning center axis RA1.

In the imaging unit 20, the turning center axis RA1 extending in the Z-axis direction is set to the vertical direction. However, the turning center axis RA1 can be set to the horizontal direction.

<Movement of One of X-Ray Generator 42 and X-Ray Detector 52>

In the above embodiment, the projection magnification factor is decreased during the confrontation by moving both the X-ray generator 42 and the X-ray detector 52 with respect to the tomographic layer of interest LOI. However, the projection magnification factor can be decreased during the confrontation by moving only one of the X-ray generator 42 and the X-ray detector 52 with respect to the tomographic layer of interest LOI.

Figure 19:
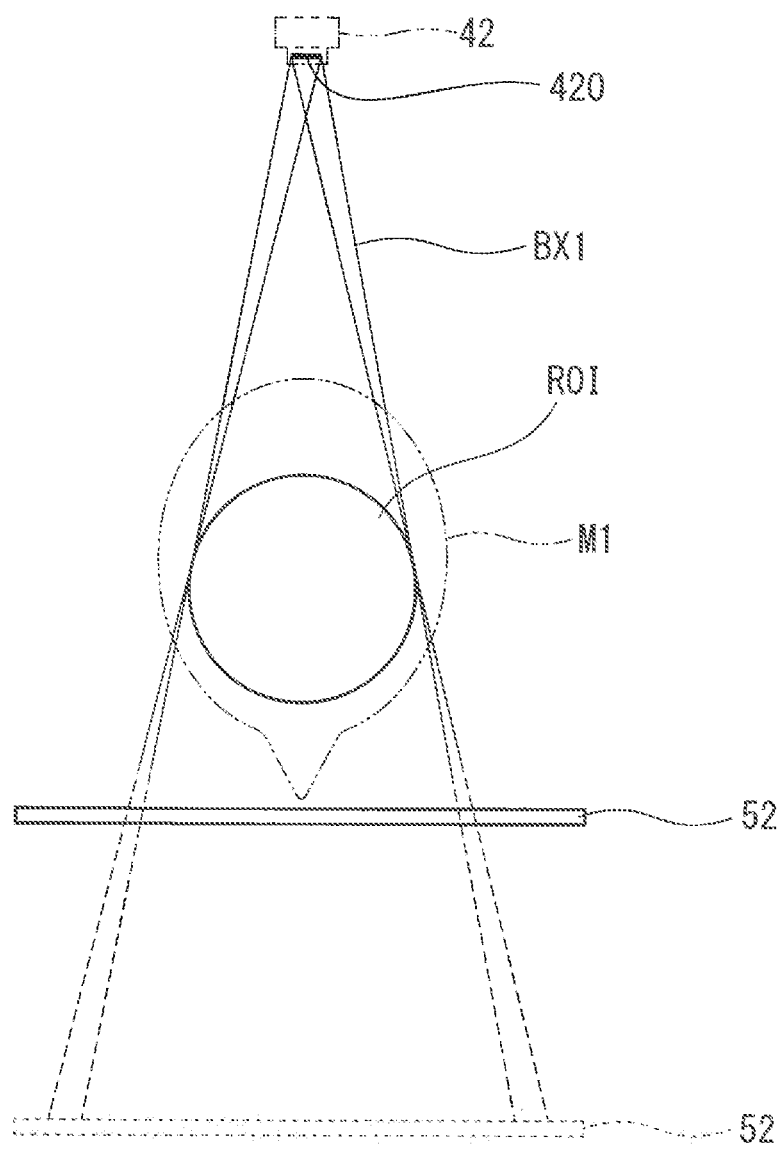
FIG. 19 is a view illustrating a state in which the projection magnification factor is decreased by moving only the X-ray detector 52.

FIG. 19 is a view illustrating a state in which the projection magnification factor is reduced by moving only the X-ray detector 52. As illustrated in FIG. 19, the projection magnification factor decreases by bringing only the X-ray detector 52 close to the imaging region ROI. Consequently, the blurring on the X-ray projection image due to the size of the focal plane 420 can be reduced.

When only the X-ray detector 52 is moved as illustrated in FIG. 19, a movement drive unit (not illustrated) that moves the X-ray detector 52 in the y-direction can be provided in the X-ray detection unit 50. The movement drive unit can be constructed with a linear motor type or ball screw type drive unit.

Figure 20:
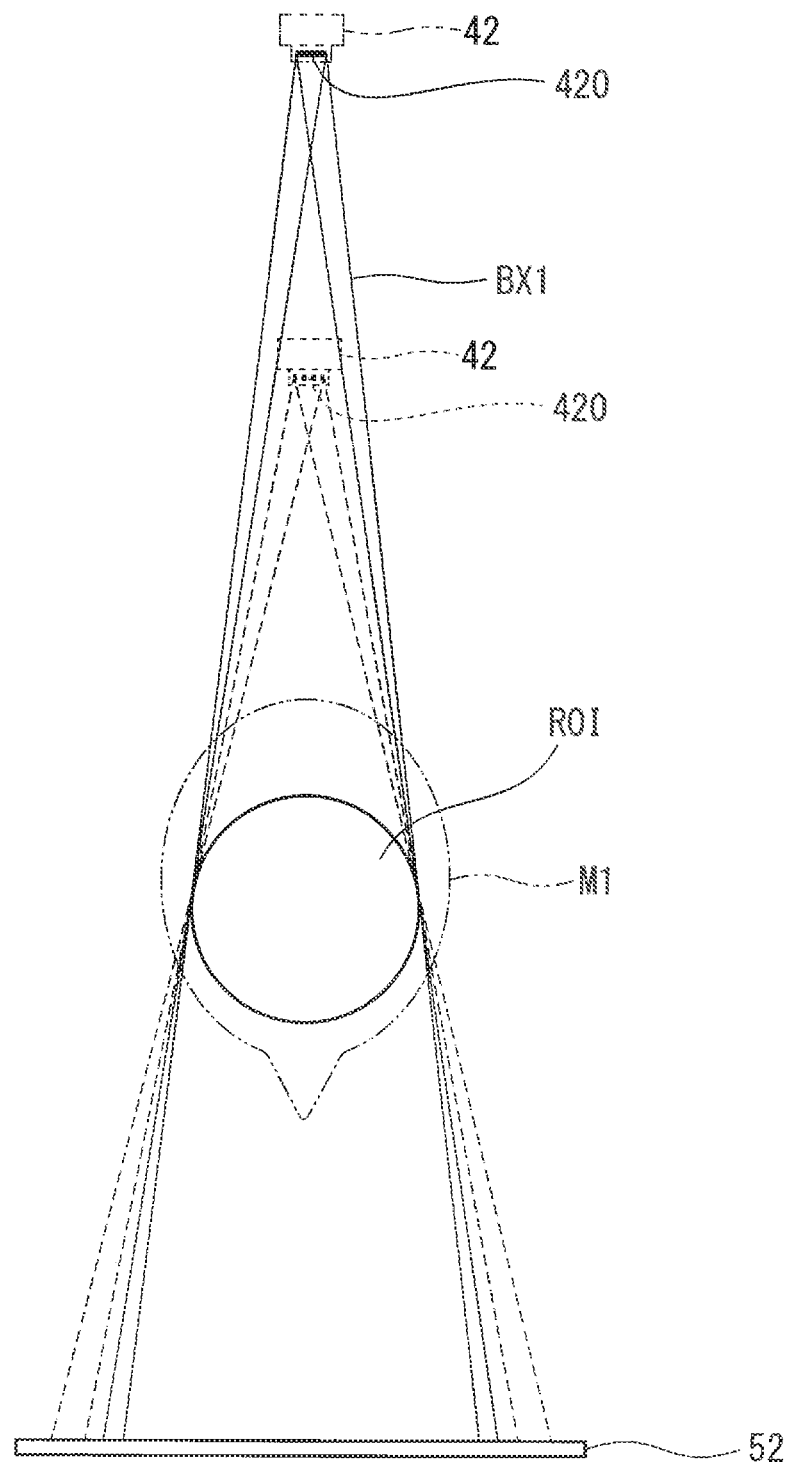
FIG. 20 is a view illustrating a state in which the projection magnification factor is decreased by moving only the X-ray generator 42.

FIG. 20 is a view illustrating a state in which the projection magnification factor is reduced by moving only the X-ray generator 42. As illustrated in FIG. 20, the projection magnification factor is decreased by moving only the X-ray generator 42 (focal plane 420) away from the imaging region ROI. Consequently, the blurring on the X-ray projection image due to the size of the focal plane 420 can be reduced. The focal plane 420 in FIGS. 19 and 20 is equivalent to the focal plane 420 in FIG. 9.

When only the X-ray generator 42 is moved, a movement drive unit that moves the entire X-ray generation unit 40 including the X-ray generator 42 in the y-direction can be provided in the turning arm 62. In this case, it is conceivable that the turning arm 62 is expandably configured.

Figure 21:
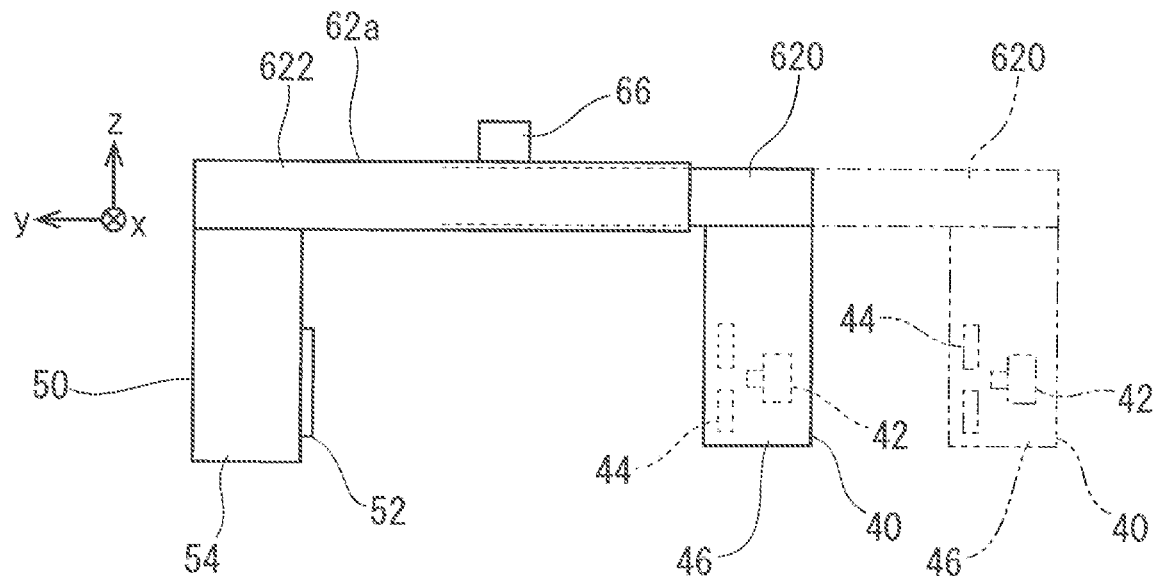
FIG. 21 is a schematic side view illustrating a turning arm 62a of the modification.

FIG. 21 is a schematic side view illustrating a turning arm 62a of the modification. As illustrated in FIG. 21, in the turning arm 62a, one end 620 supporting the X-ray generation unit 40 is configured to be accommodated inside a main body 622 of the turning arm 62. The turning arm 62a includes a movement drive unit (not illustrated) that moves the one end 620 in the y-direction. The movement drive unit accommodates the one end 620 in the main body 622, whereby the turning arm 62 is shortened and the X-ray generator 42 approaches the X-ray detector 52. The movement drive unit takes the one end 620 out of the main body 622, whereby the turning arm 62 is extended to moving the X-ray generator 42 away from the X-ray detector 52.

In the turning arm 62a of the modification, the turning arm 62a itself is expandable when the X-ray generation unit 40 is moved. When the turning arm 62a passes through a space that collides with another member during the turning, the collision can be avoided by shortening the turning arm 62a.

Figure 22:
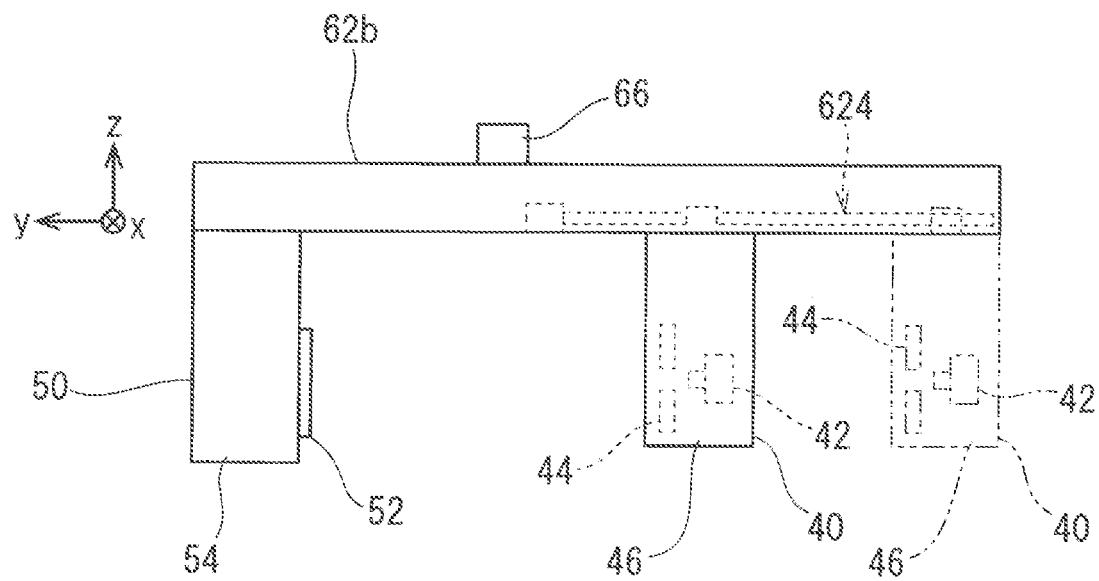
FIG. 22 is a schematic side view illustrating a turning arm 62b of the modification.

FIG. 22 is a schematic side view illustrating a turning arm 62b of the modification. The turning arm 62b includes a movement drive unit 624 that moves the X-ray generation unit 40 in the y-direction with respect to the turning arm 62. When the X-ray generator 42 confronts the tomographic layer of interest LOI during the X-ray imaging, the projection magnification factor can be decreased by moving the X-ray generator 42 in the direction in which the X-ray generator 42 is moving away from the subject M1.

For the turning arm 62b, by moving the X-ray generation unit 40 in the y-direction, the X-ray generation unit 40 can be prevented from contacting with another member during the turning. Because the turning arm 62b itself is not expandable, it is necessary that the turning arm 62b be turned such that the turning arm 62 does not contact with another member. In this respect, the turning arm 62a in FIG. 21 is more advantageous than the turning arm 62b.

Although the present invention is described in detail, the above description is illustrative in all aspects, and the present invention is not limited thereto. Innumerable modifications not illustrated can be made without departing from the scope of the present invention. The configurations described in the above embodiment and the modifications can appropriately be combined as long as they are not inconsistent with each other.

EXPLANATION OF REFERENCE SIGNS

10: X-ray tomography apparatus
20: imaging unit
30: information processor
302: imaging region setting unit
304: tomographic layer-of-interest setting unit
306: imaging trajectory setting unit
308: image processor
32: display
34: operation unit
40: X-ray generation unit
42: X-ray generator
420: focal plane
44: X-ray regulating unit
50: X-ray detection unit
52: X-ray detector
54: casing
60: support
62, 62a, 62b: turning arm
642: turning drive unit
644: XY-direction movement drive unit
66: shaft
70: post
72: subject holder
74: subject chair
80: imaging controller
802: turning controller
804: XY-direction movement controller
806: Z-direction movement controller
808: X-ray detection controller
810: X-ray generation controller
82: display
84: operation panel
ANG1: incident angle
BX1: X-ray beam
CBX1: center axis X-ray
DA1: dental arch
DN1: normal direction
LL1: center line
LOI, LOI1, LOI2: tomographic layer of interest
M1: subject
PT42: imaging trajectory
PT52: imaging trajectory
RA1: turning center axis
ROI: imaging region
SL1: tomographic plane of interest

The invention claimed is:

1. An X-ray tomography apparatus comprising:
an X-ray generator configured to emit an X-ray beam;
an X-ray detector configured to detect the X-ray beam emitted from the X-ray generator;
a support configured to support the X-ray generator and the X-ray detector;
an information processsor which performs arithmetic processing;
the information processor configured to set a tomographic layer of interest;
a turning driver configured to turn the X-ray generator and the X-ray detector relative to the tomographic layer of interest about a turning center axis set between the X-ray generator and the X-ray detector;
a movement driver configured to move at least one of the X-ray generator and the X-ray detector relative to the tomographic layer of interest in a direction perpendicular to the turning center axis;
an image processor configured to generate an X-ray tomographic image indicating the tomographic layer of interest by performing image processing on a plurality of X-ray projection images generated based on an output signal output from the X-ray detector; and a controller configured to control the turning driver and the movement driver, wherein when a center axis X-ray passing through the turning center axis in the X-ray beam is orthogonal to the tomographic layer of interest, the controller causes the X-ray detector to relatively approach the tomographic layer of interest and/or to relatively move the X-ray generator away from the tomographic layer of interest as compared to when the center axis X-ray is not orthogonal to the tomographic layer of interest.

2. The X-ray tomography apparatus according to claim 1, wherein the support includes a turning arm that supports the X-ray generator at one end side while supporting the X-ray detector at the other end side, and the turning driver is configured to turn the turning arm via a shaft, the shaft connected to a position between the X-ray generator and the X-ray detector in the turning arm.

3. The X-ray tomography apparatus according to claim 2, wherein the movement driver configured to move the shaft of the turning arm in the direction perpendicular to the turning center axis.

4. The X-ray tomography apparatus according to claim 1, wherein the controller is configured to start at least one of an approach of the X-ray detector to the tomographic layer of interest and a movement of the X-ray generator away from the tomographic layer of interest before the center axis X-ray becomes orthogonal to the tomographic layer of interest, and the controller is further configured to start at least one of a movement of the X-ray detector away from the tomographic layer of interest and an approach of the X-ray generator to the tomographic layer of interest after the center axis X-ray becomes orthogonal to the tomographic layer of interest.

5. The X-ray tomography apparatus according to claim 1, wherein the information processor is configured to set an imaging region in which a plurality of X-ray projection images are acquired by irradiation of the X-ray beam from a plurality of directions based on an input operation of designation through an input device.

6. The X-ray tomography apparatus according to claim 5, wherein the information processor is configured to set the tomographic layer of interest according to the set imaging region.

7. The X-ray tomography apparatus according to claim 6, wherein the input device is configured to receive designation of the imaging region so as to include a part of a dental arch, and the information processor is configured to set a tomographic layer along the part of the dental arch included in the imaging region as the tomographic layer of interest.

8. The X-ray tomography apparatus according to claim 1, wherein the image processor is configured to perform image processing after matching magnification factors of the plurality of X-ray projection images with each other, and generate the X-ray tomographic image.

9. The X-ray tomography apparatus according to claim 1, wherein the information processor and one of an input device or an operation panel are configured to receive designation of a tomographic thickness of the tomographic layer of interest, wherein the controller determines an incident angle when the X-ray detector is caused to approach the tomographic layer of interest according to the designated tomographic thickness.

10. An X-ray tomography method comprising:

setting a tomographic layer of interest;

turning an X-ray generator and an X-ray detector relative to the tomographic layer of interest around a turning center axis set between the X-ray generator and the X-ray detector while the tomographic layer of interest is disposed between the X-ray generator and the X-ray detector;

detecting an X-ray beam emitted from the X-ray generator using the X-ray detector;

causing, when a center axis X-ray passing through the turning center axis in the X-ray beam is orthogonal to the tomographic layer of interest, the X-ray detector to relatively approach the tomographic layer of interest and/or to relatively move the X-ray generator away from the tomographic layer of interest as compared to when the center axis X-ray is not orthogonal to the tomographic layer of interest; and performing image-processing on a plurality of X-ray projection images generated based on an output signal output from the X-ray detector, and generating an X-ray tomographic image indicating the tomographic layer of interest.

11. An X-ray tomography apparatus comprising:

an X-ray generator configured to emit an X-ray beam;

an X-ray detector configured to detect the X-ray beam emitted from the X-ray generator;

a support configured to support the X-ray generator and the X-ray detector;

an information processor which performs arithmetic processing;

the information processor configured to set a tomographic layer of interest;

a turning driver configured to turn the X-ray generator and the X-ray detector relative to the tomographic layer of interest about a turning center axis set between the X-ray generator and the X-ray detector;

a movement driver configured to move at least one of the X-ray generator and the X-ray detector relative to the tomographic layer of interest in a direction perpendicular to the turning center axis;

an image processor configured to generate an X-ray tomographic image indicating the tomographic layer of interest by performing image processing on a plurality of X-ray projection images generated based on an output signal output from the X-ray detector; and a controller configured to control the movement driver according to an incident angle while controlling the turning driver to change the incident angle of the X-ray beam with respect to the tomographic layer of interest, wherein the controller is further configured to control movement of at least one of the X-ray generator and the X-ray detector such that a magnification factor is relatively decreased in a first state in which an irradiation axis of the X-ray beam is incident on the tomographic layer of interest in a confronting manner when the first state in which the irradiation axis of the X-ray beam is incident on the tomographic layer of interest in the confronting manner and a second state in which the irradiation axis of the X-ray beam is incident on the tomographic layer of interest in a non-confronting manner are compared to each other, while the X-ray generator and the X-ray detector are turned.

* * * * *